United States Patent
Uemori et al.

(10) Patent No.: US 12,018,294 B2
(45) Date of Patent: Jun. 25, 2024

(54) DNA POLYMERASE MUTANT SUITED TO NUCLEIC ACID AMPLIFICATION FROM RNA

(71) Applicant: TAKARA BIO INC., Shiga (JP)

(72) Inventors: Takashi Uemori, Otsu (JP); Hiroyuki Matsumoto, Santa Clara, CA (US); Kensuke Saito, Kusatsu (JP); Miwa Akitomo, Kyoto (JP)

(73) Assignee: TAKARA BIO INC., Shiga (JP)

( * ) Notice: Subject to any disclaimer, the term of this patent is extended or adjusted under 35 U.S.C. 154(b) by 0 days.

(21) Appl. No.: 17/257,986

(22) PCT Filed: Jul. 3, 2019

(86) PCT No.: PCT/JP2019/026513
§ 371 (c)(1),
(2) Date: Jan. 5, 2021

(87) PCT Pub. No.: WO2020/013058
PCT Pub. Date: Jan. 16, 2020

(65) Prior Publication Data
US 2021/0222137 A1    Jul. 22, 2021

(30) Foreign Application Priority Data
Jul. 13, 2018 (JP) .................................. 2018-133086

(51) Int. Cl.
*C12N 9/12* (2006.01)

(52) U.S. Cl.
CPC .... *C12N 9/1252* (2013.01); *C12Y 207/07007* (2013.01)

(58) Field of Classification Search
None
See application file for complete search history.

(56) References Cited

U.S. PATENT DOCUMENTS

| | | | |
|---|---|---|---|
| 5,830,714 A | 11/1998 | Swaminathan et al. | |
| 7,179,590 B2 * | 2/2007 | Smith ................. | C12N 9/1252 536/23.1 |
| 8,759,061 B1 | 6/2014 | Marx et al. | |
| 2002/0012970 A1 | 1/2002 | Smith et al. | |
| 2003/0044817 A1 | 3/2003 | Laird et al. | |
| 2010/0221787 A1 | 9/2010 | Hayashizaki et al. | |
| 2013/0034879 A1 | 2/2013 | Skirgaila et al. | |
| 2013/0149748 A1 | 6/2013 | Bauer et al. | |
| 2014/0051126 A1 | 2/2014 | Bauer et al. | |
| 2014/0170730 A1 | 6/2014 | Suko | |
| 2015/0184226 A1 | 7/2015 | Bauer et al. | |
| 2017/0029792 A1 | 2/2017 | Bauer et al. | |
| 2017/0081646 A1 | 3/2017 | Skirgaila et al. | |
| 2018/0135033 A1 | 5/2018 | Bauer et al. | |
| 2018/0346889 A1 | 12/2018 | Ishino et al. | |
| 2019/0055527 A1 | 2/2019 | Ishino et al. | |

FOREIGN PATENT DOCUMENTS

| | | |
|---|---|---|
| EP | 1 152 062 | 11/2001 |
| EP | 1 201 768 | 5/2002 |
| EP | 2 554 665 | 2/2013 |
| JP | 2000-508538 | 7/2000 |
| JP | 3844975 | 9/2002 |
| JP | 2007-520227 | 7/2007 |
| JP | 2017-178804 | 10/2017 |
| JP | 2019-162106 | 9/2019 |
| WO | 2007/143436 | 12/2007 |
| WO | 2009/054510 | 4/2009 |
| WO | 2012/139748 | 10/2012 |
| WO | 2013/083264 | 6/2013 |
| WO | 2014/090836 | 6/2014 |
| WO | 2017/090684 | 6/2017 |
| WO | 2017/090685 | 6/2017 |

OTHER PUBLICATIONS

Uniprot Accession No. P52028, Jan. 31, 2018.*
Aye et al., "Engineering of DNA polymerase I from *Thermus thermophilus* using compartmentalized self-replication", Biochemical and Biophysical Research Communications, 499(9): 170-176 (2018).
Loh et al., "Mutability of DNA polymerase 1: Implications for the creation of mutant DNA polymerases", DNA Repair, 4(12): 1390-1398 (2005).
Simon et al., "Rapid Identification of Genes Encoding DNA Polymerases by Function-Based Screening of Metagenomic Libraries Derived from Glacial Ice", Applied and Environmental Microbiology, 75(9): 2964-2968 (2009).
International Preliminary Report on Patentability, dated Jan. 19, 2021 in corresponding International Patent Application No. PCT/JP2019/026513.
International Search Report, dated Oct. 1, 2019 in corresponding International Patent Application No. PCT/JP2019/026513.
Extended European Search Report dated Mar. 4, 2022 in European Patent Application No. 198333221.
Office Action dated May 9, 2023 in corresponding Japanese Patent Application No. 2020-530136, with English translation, 6 pages.

(Continued)

*Primary Examiner* — Richard G Hutson
(74) *Attorney, Agent, or Firm* — Wenderoth, Lind & Ponack, L.L.P.

(57) ABSTRACT

Provided are: a DNA polymerase mutant having reverse transcriptase activity, the DNA polymerase mutant including a sequence consisting of twelve specific amino acids A1-A12, wherein the DNA polymerase mutant having reverse transcriptase activity is characterized in that the A3 and/or A10 amino acid is substituted by a basic amino acid residue different from that prior to the introduction of mutation; a kit and a composition including the DNA polymerase; a method for producing the DNA polymerase; and a method for modifying an existing DNA polymerase having reverse transcriptase activity.

5 Claims, No Drawings
Specification includes a Sequence Listing.

(56) References Cited

OTHER PUBLICATIONS

Communication pursuant to Article 94(3) EPC dated Dec. 1, 2022 in European Patent Application No. 19 833 322.1.
Office Action dated Jun. 16, 2023 in corresponding European Patent Application No. 19833322.1.
Office Action with the Search Report dated Aug. 23, 2023 in corresponding Chinese Patent Application No. 201980046835.1, with English-language translation.

* cited by examiner

SEQUENCE LISTING

<160> NUMBER OF SEQ ID NOS: 28

<210> SEQ ID NO 1
<211> LENGTH: 834
<212> TYPE: PRT
<213> ORGANISM: Thermus thermophilus

<400> SEQUENCE: 1

```
Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Ala Pro Ala Pro Leu Glu Glu Ala Pro Trp Pro Pro Pro
    290                 295                 300
```

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
            325                 330                 335

Ala Ala Asp Pro Leu Ala Gly Leu Lys Asp Leu Lys Val Arg Gly
        340                 345                 350

Leu Leu Ala Lys Asp Leu Ala Val Leu Ala Ser Arg Glu Gly Leu Asp
            355                 360                 365

Leu Val Pro Gly Asp Pro Met Leu Leu Ala Tyr Leu Leu Asp Pro
        370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
            405                 410                 415

Asn Leu Leu Lys Arg Leu Glu Gly Glu Glu Lys Leu Leu Trp Leu Tyr
            420                 425                 430

His Glu Val Glu Lys Pro Leu Ser Arg Val Leu Ala His Met Glu Ala
            435                 440                 445

Thr Gly Val Arg Leu Asp Val Ala Tyr Leu Gln Ala Leu Ser Leu Glu
            450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
            515                 520                 525

Pro Ile Val Glu Lys Ile Leu Gln His Arg Glu Leu Thr Lys Leu Lys
        530                 535                 540

Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
            565                 570                 575

Ser Ser Ser Asp Pro Asn Leu Gln Asn Ile Pro Val Arg Thr Pro Leu
        580                 585                 590

Gly Gln Arg Ile Arg Arg Ala Phe Val Ala Glu Ala Gly Trp Ala Leu
        595                 600                 605

Val Ala Leu Asp Tyr Ser Gln Ile Glu Leu Arg Val Leu Ala His Leu
        610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
            645                 650                 655

Asp Pro Leu Met Arg Arg Ala Ala Lys Thr Val Asn Phe Gly Val Leu
        660                 665                 670

Tyr Gly Met Ser Ala His Arg Leu Ser Gln Glu Leu Ala Ile Pro Tyr
        675                 680                 685

Glu Glu Ala Val Ala Phe Ile Glu Arg Tyr Phe Gln Ser Phe Pro Lys
        690                 695                 700

Val Arg Ala Trp Ile Glu Lys Thr Leu Glu Glu Gly Arg Lys Arg Gly
705                 710                 715                 720

-continued

```
Tyr Val Glu Thr Leu Phe Gly Arg Arg Tyr Val Pro Asp Leu Asn
            725                 730                 735

Ala Arg Val Lys Ser Val Arg Glu Ala Ala Glu Arg Met Ala Phe Asn
        740                 745                 750

Met Pro Val Gln Gly Thr Ala Ala Asp Leu Met Lys Leu Ala Met Val
            755                 760                 765

Lys Leu Phe Pro Arg Leu Arg Glu Met Gly Ala Arg Met Leu Leu Gln
    770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Met Gly Glu Asp Trp Leu Ser Ala
            820                 825                 830

Lys Gly

<210> SEQ ID NO 2
<211> LENGTH: 23
<212> TYPE: DNA
<213> ORGANISM: Artificial Sequence
<220> FEATURE:
<223> OTHER INFORMATION: PCR forward Primer lambda RNA

<400> SEQUENCE: 2
caggtggcgt attccagatt gtc                                             23

<210> SEQ ID NO 3
<211> LENGTH: 20
<212> TYPE: DNA
<213> ORGANISM: Artificial Sequence
<220> FEATURE:
<223> OTHER INFORMATION: PCR Reverse Primer lambda RNA

<400> SEQUENCE: 3
gcaccatact ggcaccgaga                                                 20

<210> SEQ ID NO 4
<211> LENGTH: 18
<212> TYPE: DNA
<213> ORGANISM: Artificial Sequence
<220> FEATURE:
<223> OTHER INFORMATION: Probe lambda RNA. 5'-end is labeled FAM and
      3'-end is labeled BHQ1

<400> SEQUENCE: 4
accaccggcc ccaatggc                                                   18

<210> SEQ ID NO 5
<211> LENGTH: 834
<212> TYPE: PRT
<213> ORGANISM: Artificial Sequence
<220> FEATURE:
<223> OTHER INFORMATION: DNA polymerase variant Tth b13

<400> SEQUENCE: 5

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45
```

```
Lys Ser Leu Leu Lys Ala Leu Lys Glu Asp Gly Tyr Lys Ala Val Phe
    50              55                  60

Val Val Phe Asp Ala Lys Ala Pro Ser Phe Arg His Glu Ala Tyr Glu
65              70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Gly Phe Thr Arg Leu
                100                 105                 110

Glu Val Pro Gly Tyr Glu Ala Asp Val Leu Ala Thr Leu Ala Lys
            115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
            195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
    275                 280                 285

Leu Leu Glu Ala Pro Ala Pro Leu Glu Glu Ala Pro Trp Pro Pro Pro
    290                 295                 300

Gly Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
            325                 330                 335

Ala Ala Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
    355                 360                 365

Leu Val Pro Gly Asp Asp Pro Met Leu Leu Ala Tyr Leu Leu Asp Pro
    370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
                405                 410                 415

Asn Leu Leu Lys Arg Leu Glu Gly Glu Glu Lys Leu Leu Trp Leu Tyr
            420                 425                 430

His Glu Val Glu Lys Pro Leu Ser Arg Val Leu Ala His Met Glu Ala
                435                 440                 445

Thr Gly Val Arg Leu Asp Val Ala Tyr Leu Gln Ala Leu Ser Leu Glu
    450                 455                 460

Leu Ala Glu Glu Ile Arg Arg Leu Glu Glu Glu Val Phe Arg Leu Ala
```

-continued

```
      465                 470                 475                 480
Gly His Pro Phe Asn Leu Asn Ser Arg Asp Gln Leu Glu Arg Val Leu
                    485                 490                 495
Phe Asp Glu Leu Arg Leu Pro Ala Leu Gly Lys Thr Gln Lys Thr Gly
                500                 505                 510
Lys Arg Ser Thr Ser Ala Ala Val Leu Glu Ala Leu Arg Glu Ala His
                515                 520                 525
Pro Ile Val Glu Lys Ile Leu Gln His Arg Glu Leu Thr Lys Leu Lys
            530                 535                 540
Asn Thr Tyr Val Asp Pro Leu Pro Ser Leu Val His Pro Arg Thr Gly
545                 550                 555                 560
Arg Leu His Thr Arg Phe Asn Gln Thr Ala Thr Ala Thr Gly Arg Leu
                    565                 570                 575
Ser Ser Ser Asp Pro Asn Leu Gln Asn Ile Pro Val Arg Thr Pro Leu
                580                 585                 590
Gly Gln Arg Ile Arg Arg Ala Phe Val Ala Glu Ala Gly Trp Ala Leu
                595                 600                 605
Val Ala Leu Asp Tyr Ser Gln Ile Glu Leu Arg Val Leu Ala His Leu
            610                 615                 620
Ser Gly Asp Glu Asn Leu Ile Arg Val Phe Gln Glu Gly Lys Asp Ile
625                 630                 635                 640
His Thr Gln Thr Ala Ser Trp Met Phe Gly Val Pro Pro Glu Ala Val
                    645                 650                 655
Asp Pro Leu Met Arg Arg Ala Ala Lys Thr Val Asn Phe Gly Val Leu
                660                 665                 670
Tyr Gly Met Ser Ala His Arg Leu Ser Arg Glu Leu Ala Ile Pro Tyr
                675                 680                 685
Glu Glu Ala Val Ala Phe Ile Glu Arg Tyr Phe Gln Ser Phe Pro Lys
            690                 695                 700
Val Arg Ala Trp Ile Glu Lys Thr Leu Glu Glu Gly Arg Lys Arg Gly
705                 710                 715                 720
Tyr Val Glu Thr Leu Phe Gly Arg Arg Arg Tyr Val Pro Asp Leu Asn
                    725                 730                 735
Ala Arg Val Lys Ser Val Arg Glu Ala Ala Glu Arg Met Ala Phe Asn
                740                 745                 750
Met Pro Val Gln Gly Thr Ala Ala Asp Leu Met Lys Leu Ala Met Val
                755                 760                 765
Lys Leu Phe Pro Arg Leu Arg Glu Met Gly Ala Arg Met Leu Leu Gln
            770                 775                 780
Val His Asp Glu Leu Leu Leu Glu Ala Pro Gln Ala Arg Ala Glu Glu
785                 790                 795                 800
Val Ala Ala Leu Ala Lys Glu Ala Met Glu Lys Ala Tyr Pro Leu Ala
                    805                 810                 815
Val Pro Leu Glu Val Glu Val Gly Met Gly Glu Asp Trp Leu Ser Ala
                820                 825                 830
Lys Gly

<210> SEQ ID NO 6
<211> LENGTH: 2505
<212> TYPE: DNA
<213> ORGANISM: Artificial Sequence
<220> FEATURE:
<223> OTHER INFORMATION: DNA polymerase variant Tth b13

<400> SEQUENCE: 6
```

```
atggaagcta tgctgccgct gttcgaaccg aaaggtcgtg ttctgctggt tgacggtcac    60
cacctggctt accgtacctt cttcgctctg aaaggtctga ccacctctcg tggtgaaccg   120
gttcaggctg tttacggttt cgctaaatct ctgctgaaag ctctgaaaga gatggttac   180
aaagctgttt tcgttgtatt cgacgcgaaa gctccgtctt ccgtcacga gcttacgaa    240
gcttacaaag ctggtcgtgc tccgaccccg aagacttcc cgcgtcagct ggctctgatc   300
aaagaactgt tgacctgct gggtttcacc cgtctggaag ttccgggtta cgaagctgac   360
gacgttctgg ctaccctggc taaaaaagct gaaaagaag gttacgaagt cgtatcctg    420
accgctgacc gtgacctgta ccagctggtt tctgaccgtg ttgctgttct gcacccggaa   480
ggtcacctga tcaccccgga atggctgtgg gaaaaatacg gtctgcgtcc ggaacagtgg   540
gttgacttcc gtgctctggt tggtgacccg tctgacaacc tgccgggtgt taaaggtatc   600
ggtgaaaaaa ccgctctgaa actgctgaaa gaatggggtt ctctggaaaa cctgctgaaa   660
aacctggacc gtgttaaacc ggaaaacgtt cgtgaaaaaa tcaaagctca cctggaagac   720
ctgcgtctgt ctctggaact gtctcgtgtt cgtaccgacc tgccgctgga agttgacctg   780
gctcagggtc gtgaaccgga ccgtgaaggt ctgcgtgctt cctggaacg tctggaattc   840
ggttctctgc tgcacgaatt cggtctgctg aagctccgg ctccgctgga agaagctccg   900
tggccgcccc cggagggtgc gttcgtcggc ttcgttctgt ctcgtccgga accgatgtgg   960
gctgaactga agctctggc tgcttgccgt gacggtcgtg ttcaccgtgc tgctgacccg  1020
ctggctggtc tgaaagacct gaaagaagtt cgtggtctgc tggctaaaga cctggctgtt  1080
ctggcttctc gtgaaggtct ggacctggtt ccgggtgacg accgatgct gctggcttac  1140
ctgctggacc cgtctaacac caccccggaa ggtgttgctc gtcgttacgg tggtgaatgg  1200
accgaagacg ctgctcaccg tgctctgctg tctgaacgtc tgcaccgtaa cctgctgaaa  1260
cgtctggaag gtgaagaaaa actgctgtgg ctgtaccacg aagttgaaaa accgctgtct  1320
cgtgttctgg ctcacatgga agctaccggt gttcgtctgg acgttgctta cctgcaggct  1380
ctgtctctgg aactggctga gaaatccgt cgtctggaag aagaagtttt ccgtctggct  1440
ggtcacccgt tcaacctgaa ctctcgtgac cagctggaac gtgttctgtt cgacgaactg  1500
cgtctgccgg ctctgggtaa aacccagaaa ccggtaaac gttctacctc tgctgctgtt  1560
ctggaagctc tgcgtgaagc tcacccgatc gttgaaaaaa tcctgcagca ccgtgaactg  1620
accaaactga aaacaccta cgttgacccg ctgccgtctc tggttcaccc gcgtaccggt  1680
cgtctgcaca cccgttcaa ccagaccgct accgctaccg tcgtctgtc ttcttctgac  1740
ccgaacctgc agaacatccc ggttcgtacc ccgctgggtc agcgtatccg tcgtgctttc  1800
gttgctgaag ctggttgggc tctggttgct ctggactact ctcagatcga actgcgtgtt  1860
ctggctcacc tgtctggtga cgaaaacctg atccgtgttt tccaggaagg taaagacatc  1920
cacacccaga ccgcttcttg gatgttcggt gttccgccgg aagctgttga cccgctgatg  1980
cgtcgtgctg ctaaaaccgt taacttcggt gttctgtacg gtatgtctgc tcaccgtctg  2040
tctcgtgaac tggctatccc gtacgaagaa gctgttgctt tcatcgaacg ttacttccag  2100
tctttcccga aagttcgtgc ttggatcgaa aaaaccctgg aagaaggtcg taaacgtggt  2160
tacgttgaaa ccctgttcgg tcgtcgtcgt tacgttccgg acctgaacgc tcgtgttaaa  2220
tctgttcgtg aagctgctga acgtatggct ttcaacatgc cggttcaggg taccgctgct  2280
gacctgatga aactggctat ggttaaactg ttcccgcgtc tgcgtgaaat gggtgctcgt  2340
```

```
atgctgctgc aggttcacga cgaactgctg ctggaagctc cgcaggctcg tgctgaagaa    2400
gttgctgctc tggctaaaga agctatggaa aaagcttacc cgctggctgt tccgctggaa    2460
gttgaagttg gtatgggtga agactggctg tctgctaaag gttaa                    2505
```

<210> SEQ ID NO 7
<211> LENGTH: 834
<212> TYPE: PRT
<213> ORGANISM: Artificial Sequence
<220> FEATURE:
<223> OTHER INFORMATION: DNA polymerase variant Tth b46

<400> SEQUENCE: 7

```
Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Ala Pro Ala Pro Leu Glu Glu Ala Pro Trp Pro Pro Pro
    290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335
```

```
Ala Ala Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
            355                 360                 365

Leu Val Pro Gly Asp Asp Pro Met Leu Leu Ala Tyr Leu Leu Asp Pro
        370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
                405                 410                 415

Asn Leu Leu Lys Arg Leu Glu Gly Glu Glu Lys Leu Leu Trp Leu Tyr
            420                 425                 430

His Glu Val Glu Lys Pro Leu Ser Arg Val Leu Ala His Met Glu Ala
            435                 440                 445

Thr Gly Val Arg Leu Asp Val Ala Tyr Leu Gln Ala Leu Ser Leu Glu
        450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
            485                 490                 495

Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
            515                 520                 525

Pro Ile Val Glu Lys Ile Leu Gln His Arg Glu Leu Thr Lys Leu Lys
        530                 535                 540

Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
            595                 600                 605

Val Ala Leu Asp Tyr Ser Gln Ile Glu Leu Arg Val Leu Ala His Leu
        610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
                645                 650                 655

Asp Pro Leu Met Arg Arg Ala Ala Lys Thr Val Asn Phe Gly Val Leu
            660                 665                 670

Tyr Gly Met Ser Ala His Arg Leu Ser Gln Glu Leu Ala Ile Pro Tyr
        675                 680                 685

Arg Glu Ala Val Ala Phe Ile Glu Arg Tyr Phe Gln Ser Phe Pro Lys
            690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Tyr Val Pro Asp Leu Asn
                725                 730                 735

Ala Arg Val Lys Ser Val Arg Glu Ala Ala Glu Arg Met Ala Phe Asn
            740                 745                 750

Met Pro Val Gln Gly Thr Ala Ala Asp Leu Met Lys Leu Ala Met Val
```

```
                755                 760                 765
Lys Leu Phe Pro Arg Leu Arg Glu Met Gly Ala Arg Met Leu Leu Gln
         770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                 805                 810                 815

Val Pro Leu Glu Val Glu Val Gly Met Gly Glu Asp Trp Leu Ser Ala
         820                 825                 830

Lys Gly
```

<210> SEQ ID NO 8
<211> LENGTH: 2505
<212> TYPE: DNA
<213> ORGANISM: Artificial Sequence
<220> FEATURE:
<223> OTHER INFORMATION: DNA polymerase variant Tth b46

<400> SEQUENCE: 8

```
atggaagcta tgctgccgct gttcgaaccg aaaggtcgtg ttctgctggt tgacggtcac      60
cacctggctt accgtacctt cttcgctctg aaaggtctga ccacctctcg tggtgaaccg     120
gttcaggctg tttacggttt cgctaaatct ctgctgaaag ctctgaaaga agatggttac     180
aaagctgttt tcgttgtatt cgacgcgaaa gctccgtctt ccgtcacga gcttacgaa      240
gcttacaaag ctggtcgtgc tccgaccccg aagacttcc cgcgtcagct ggctctgatc     300
aaagaactgg ttgacctgct gggtttcacc cgtctggaag ttccgggtta cgaagctgac     360
gacgttctgg ctaccctggc taaaaaagct gaaaagaag gttacgaagt cgtatcctg      420
accgctgacc gtgacctgta ccagctggtt tctgaccgtg ttgctgttct gcacccggaa     480
ggtcacctga tcacccggga atggctgtgg aaaaatacg gtctgcgtcc ggaacagtgg     540
gttgacttcc gtgctctggt tggtgacccg ctgacaacc tgccgggtgt aaaggtatc      600
ggtgaaaaaa ccgctctgaa actgctgaaa gaatggggtt ctctggaaaa cctgctgaaa     660
aacctggacc gtgttaaacc ggaaaacgtt cgtgaaaaaa tcaaagctca cctggaagac     720
ctgcgtctgt ctctggaact gtctcgtgtt cgtaccgacc tgccgctgga agttgacctg     780
gctcagggtc gtgaaccgga ccgtgaaggt ctgcgtgctt cctggaacg tctgaattc      840
ggttctctgc tgcacgaatt cggtctgctg gaagctccgg ctccgctgga agaagctccg     900
tggccgcccc cggagggtgc gttcgtcggc ttcgttctgt ctcgtccgga accgatgtgg     960
gctgaactga agctctggc tgcttgccgt gacggtcgtg ttcaccgtgc tgctgacccg    1020
ctggctggtc tgaaagacct gaagaagtt cgtggtctgc tggctaaaga cctggctgtt    1080
ctggcttctc gtgaaggtct ggacctggtt ccgggtgacg accgatgct gctggcttac    1140
ctgctggacc cgtctaacac cacccggaa ggtgttgctc gtcgttacgg tggtgaatgg    1200
accgaagacg ctgctcaccg tgctctgctg tctgaacgtc tgcaccgtaa cctgctgaaa    1260
cgtctggaag gtgaagaaaa actgctgtgg ctgtaccacg aagttgaaaa accgctgtct    1320
cgtgttctgg ctcacatgga agctaccggt gttcgtctgg acgttgctta cctgcaggct    1380
ctgtctctgg aactggctga gaaatccgt cgtctggaag aagaagtttt ccgtctggct    1440
ggtcacccgt tcaacctgaa ctctcgtgac cagctggaac gtgttctgtt cgacgaactg    1500
cgtctgccgg ctctgggtaa aacccagaaa accggtaaac gttctacctc tgctgctgtt    1560
ctggaagctc tgcgtgaagc tcacccgatc gttgaaaaaa tcctgcagca ccgtgaactg    1620
```

```
accaaactga aaaacaccta cgttgacccg ctgccgtctc tggttcaccc gcgtaccggt    1680
cgtctgcaca cccgtttcaa ccagaccgct accgctaccg gtcgtctgtc ttcttctgac    1740
ccgaacctgc agaacatccc ggttcgtacc ccgctgggtc agcgtatccg tcgtgctttc    1800
gttgctgaag ctggttgggc tctggttgct ctggactact ctcagatcga actgcgtgtt    1860
ctggctcacc tgtctggtga cgaaaacctg atccgtgttt ccaggaagg taaagacatc    1920 cacacccaga ccgcttcttg gatgttcggt gttccgccgg aagctgttga cccgctgatg    1980
cgtcgtgctg ctaaaaccgt taacttcggt gttctgtacg gtatgtctgc tcaccgtctg    2040
tctcaggaac tggctatccc gtaccgtgaa gctgttgctt tcatcgaacg ttacttccag    2100
tctttcccga agttcgtgc ttggatcgaa aaaccctgg aagaaggtcg taaacgtggt    2160
tacgttgaaa ccctgttcgg tcgtcgtcgt acgttccgg acctgaacgc tcgtgttaaa    2220
tctgttcgtg aagctgctga acgtatggct ttcaacatgc cggttcaggg taccgctgct    2280
gacctgatga aactggctat ggttaaactg ttcccgcgtc tgcgtgaaat gggtgctcgt    2340
atgctgctgc aggttcacga cgaactgctg ctggaagctc cgcaggctcg tgctgaagaa    2400
gttgctgctc tggctaaaga agctatgaaa aaagcttacc cgctggctgt tccgctggaa    2460
gttgaagttg gtatgggtga agactggctg tctgctaaag gttaa              2505
```

<210> SEQ ID NO 9
<211> LENGTH: 834
<212> TYPE: PRT
<213> ORGANISM: Artificial Sequence
<220> FEATURE:
<223> OTHER INFORMATION: DNA polymerase variant Tth b13 b46

<400> SEQUENCE: 9

```
Met Glu Ala Met Leu Pro Leu Phe Glu Pro Lys Gly Arg Val Leu Leu
  1               5                  10                  15

Val Asp Gly His His Leu Ala Tyr Arg Thr Phe Phe Ala Leu Lys Gly
             20                  25                  30

Leu Thr Thr Ser Arg Gly Glu Pro Val Gln Ala Val Tyr Gly Phe Ala
         35                  40                  45

Lys Ser Leu Leu Lys Ala Leu Lys Glu Asp Gly Tyr Lys Ala Val Phe
     50                  55                  60

Val Val Phe Asp Ala Lys Ala Pro Ser Phe Arg His Glu Ala Tyr Glu
 65                  70                  75                  80

Ala Tyr Lys Ala Gly Arg Ala Pro Thr Pro Glu Asp Phe Pro Arg Gln
                 85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205
```

```
Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Ala Pro Ala Pro Leu Glu Glu Ala Pro Trp Pro Pro Pro
    290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Ala Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
        355                 360                 365

Leu Val Pro Gly Asp Asp Pro Met Leu Leu Ala Tyr Leu Leu Asp Pro
    370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
                405                 410                 415

Asn Leu Leu Lys Arg Leu Glu Gly Glu Glu Lys Leu Leu Trp Leu Tyr
            420                 425                 430

His Glu Val Glu Lys Pro Leu Ser Arg Val Leu Ala His Met Glu Ala
        435                 440                 445

Thr Gly Val Arg Leu Asp Val Ala Tyr Leu Gln Ala Leu Ser Leu Glu
    450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
        515                 520                 525

Pro Ile Val Glu Lys Ile Leu Gln His Arg Glu Leu Thr Lys Leu Lys
    530                 535                 540

Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
        595                 600                 605

Val Ala Leu Asp Tyr Ser Gln Ile Glu Leu Arg Val Leu Ala His Leu
    610                 615                 620
```

```
Ser Gly Asp Glu Asn Leu Ile Arg Val Phe Gln Gly Lys Asp Ile
625                 630                 635                 640

His Thr Gln Thr Ala Ser Trp Met Phe Gly Val Pro Pro Glu Ala Val
            645                 650                 655

Asp Pro Leu Met Arg Arg Ala Ala Lys Thr Val Asn Phe Gly Val Leu
                660                 665                 670

Tyr Gly Met Ser Ala His Arg Leu Ser Arg Glu Leu Ala Ile Pro Tyr
            675                 680                 685

Arg Glu Ala Val Ala Phe Ile Glu Arg Tyr Phe Gln Ser Phe Pro Lys
        690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Tyr Val Pro Asp Leu Asn
                725                 730                 735

Ala Arg Val Lys Ser Val Arg Glu Ala Ala Glu Arg Met Ala Phe Asn
                740                 745                 750

Met Pro Val Gln Gly Thr Ala Ala Asp Leu Met Lys Leu Ala Met Val
            755                 760                 765

Lys Leu Phe Pro Arg Leu Arg Glu Met Gly Ala Arg Met Leu Leu Gln
770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Met Gly Glu Asp Trp Leu Ser Ala
            820                 825                 830

Lys Gly

<210> SEQ ID NO 10
<211> LENGTH: 2505
<212> TYPE: DNA
<213> ORGANISM: Artificial Sequence
<220> FEATURE:
<223> OTHER INFORMATION: DNA polymerase variant Tth b13 b46

<400> SEQUENCE: 10
atggaagcta tgctgccgct gttcgaaccg aaaggtcgtg ttctgctggt tgacggtcac      60
cacctggctt accgtacctt cttcgctctg aaaggtctga ccacctctcg tggtgaaccg     120
gttcaggctg tttacggttt cgctaaatct ctgctgaaag ctctgaaaga agatggttac     180
aaagctgttt tcgttgtatt cgacgcgaaa gctccgtctt ccgtcacga agcttacgaa     240 gcttacaaag ctggtcgtgc tccgaccccg aagacttcc gcgtcagct ggctctgatc     300 aaagaactgg ttgacctgct gggtttcacc cgtctggaag ttccgggtta cgaagctgac     360
gacgttctgg ctaccctggc taaaaaagct gaaaagaag gttacgaagt cgtatcctg     420 accgctgacc gtgaccctgta ccagctggtt tctgaccgtg ttgctgttct gcacccggaa     480
ggtcacctga tcaccccgga atggctgtgg gaaaaatacg gtctgcgtcc ggaacagtgg     540
gttgacttcc gtgctctggt tggtgacccg tctgacaacc tgccgggtgt taaaggtatc     600
ggtgaaaaaa ccgctctgaa actgctgaaa gaatggggt tctctggaaaa cctgctgaaa     660 aacctggacc gtgttaaacc ggaaaacgtt cgtgaaaaaa tcaaagctca cctggaagac     720
ctgcgtctgt ctctggaact gtctcgtgtt cgtaccgacc tgccgctgga agttgacctg     780
gctcagggtc gtgaaccgga ccgtgaaggt ctgcgtgctt cctgaacg tctggaattc     840
```

-continued

```
ggttctctgc tgcacgaatt cggtctgctg gaagctccgg ctccgctgga agaagctccg   900
tggccgcccc cggagggtgc gttcgtcggc ttcgttctgt ctcgtccgga accgatgtgg   960
gctgaactga aagctctggc tgcttgccgt gacggtcgtg ttcaccgtgc tgctgacccg  1020
ctggctggtc tgaaagacct gaaagaagtt cgtggtctgc tggctaaaga cctggctgtt  1080
ctggcttctc gtgaaggtct ggacctggtt ccgggtgacg acccgatgct gctggcttac  1140
ctgctggacc cgtctaacac caccccggaa ggtgttgctc gtcgttacgg tggtgaatgg  1200
accgaagacg ctgctcaccg tgctctgctg tctgaacgtc tgcaccgtaa cctgctgaaa  1260
cgtctggaag gtgaagaaaa actgctgtgg ctgtaccacg aagttgaaaa accgctgtct  1320
cgtgttctgg ctcacatgga agctaccggt gttcgtctgg acgttgctta cctgcaggct  1380
ctgtctctgg aactggctga gaaatccgt cgtctggaag aagaagtttt ccgtctggct  1440
ggtcacccgt tcaacctgaa ctctcgtgac cagctggaac gtgttctgtt cgacgaactg  1500
cgtctgccgg ctctgggtaa aacccagaaa accggtaaac gttctacctc tgctgctgtt  1560
ctggaagctc tgcgtgaagc tcacccgatc gttgaaaaaa tcctgcagca ccgtgaactg  1620
accaaactga aaacaccta cgttgacccg ctgccgtctc tggttcaccc gcgtaccggt  1680
cgtctgcaca cccgtttcaa ccagaccgct accgctaccg tcgtctgtc ttcttctgac  1740
ccgaacctgc agaacatccc ggttcgtacc ccgctgggtc agcgtatccg tcgtgctttc  1800
gttgctgaag ctggttgggc tctggttgct ctggactact ctcagatcga actgcgtgtt  1860
ctggctcacc tgtctggtga cgaaaacctg atccgtgttt ccaggaagg taaagacatc  1920
cacacccaga ccgcttcttg gatgttcggt gttccgccgg aagctgttga cccgctgatg  1980
cgtcgtgctg ctaaaaccgt taacttcggt gttctgtacg gtatgtctgc tcaccgtctg  2040
tctcgtgaac tggctatccc gtaccgtgaa gctgttgctt catcgaacg ttacttccag  2100
tcttcccga agttcgtgc ttggatcgaa aaaccctgg aagaaggtcg taaacgtggt  2160
tacgttgaaa ccctgttcgg tcgtcgtcgt tacgttccgg acctgaacgc tcgtgttaaa  2220
tctgttcgtg aagctgctga acgtatggct ttcaacatgc cggttcaggg taccgctgct  2280
gacctgatga aactggctat ggttaaactg ttcccgcgtc tgcgtgaaat gggtgctcgt  2340
atgctgctgc aggttcacga cgaactgctg ctggaagctc gcaggctcg tgctgaagaa  2400
gttgctgctc tggctaaaga agctatgaaa aaagcttacc cgctggctgt tccgctggaa  2460
gttgaagttg gtatgggtga agactggctg tctgctaaag gttaa              2505
```

<210> SEQ ID NO 11
<211> LENGTH: 911
<212> TYPE: PRT
<213> ORGANISM: Artificial Sequence
<220> FEATURE:
<223> OTHER INFORMATION: PIP-L14-PIP-L14-PIP-L15 Tth

<400> SEQUENCE: 11

```
Met Ser Gly Lys Gln Ala Thr Leu Phe Asp Phe Leu Lys Ser Gly Ser
1               5                   10                  15

Gly Ser Gly Ser Gly Ser Gly Ser Gly Ser Gly Lys Gln Ala Thr Leu
            20                  25                  30

Phe Asp Phe Leu Lys Ser Gly Ser Gly Ser Gly Ser Gly Ser Gly Ser
        35                  40                  45

Gly Ser Gly Lys Gln Ala Thr Leu Phe Asp Phe Leu Lys Lys Gly Ser
    50                  55                  60

Gly Ser Gly Ser Gly Ser Gly Ser Gly Ser Gly Ser Gly Met Glu Ala
```

```
                65                  70                  75                  80
            Met Leu Pro Leu Phe Glu Pro Lys Gly Arg Val Leu Leu Val Asp Gly
                                85                  90                  95

His His Leu Ala Tyr Arg Thr Phe Ala Leu Lys Gly Leu Thr Thr
                            100                 105                 110

Ser Arg Gly Glu Pro Val Gln Ala Val Tyr Gly Phe Ala Lys Ser Leu
                        115                 120                 125

Leu Lys Ala Leu Lys Glu Asp Gly Tyr Lys Ala Val Phe Val Val Phe
            130                 135                 140

Asp Ala Lys Ala Pro Ser Phe Arg His Glu Ala Tyr Glu Ala Tyr Lys
            145                 150                 155                 160

Ala Gly Arg Ala Pro Thr Pro Glu Asp Phe Pro Arg Gln Leu Ala Leu
                            165                 170                 175

Ile Lys Glu Leu Val Asp Leu Leu Gly Phe Thr Arg Leu Glu Val Pro
                        180                 185                 190

Gly Tyr Glu Ala Asp Asp Val Leu Ala Thr Leu Ala Lys Lys Ala Glu
                    195                 200                 205

Lys Glu Gly Tyr Glu Val Arg Ile Leu Thr Ala Asp Arg Asp Leu Tyr
                210                 215                 220

Gln Leu Val Ser Asp Arg Val Ala Val Leu His Pro Glu Gly His Leu
            225                 230                 235                 240

Ile Thr Pro Glu Trp Leu Trp Glu Lys Tyr Gly Leu Arg Pro Glu Gln
                            245                 250                 255

Trp Val Asp Phe Arg Ala Leu Val Gly Asp Pro Ser Asp Asn Leu Pro
                        260                 265                 270

Gly Val Lys Gly Ile Gly Glu Lys Thr Ala Leu Lys Leu Leu Lys Glu
                    275                 280                 285

Trp Gly Ser Leu Glu Asn Leu Leu Lys Asn Leu Asp Arg Val Lys Pro
                290                 295                 300

Glu Asn Val Arg Glu Lys Ile Lys Ala His Leu Glu Asp Leu Arg Leu
            305                 310                 315                 320

Ser Leu Glu Leu Ser Arg Val Arg Thr Asp Leu Pro Leu Glu Val Asp
                            325                 330                 335

Leu Ala Gln Gly Arg Glu Pro Asp Arg Glu Gly Leu Arg Ala Phe Leu
                        340                 345                 350

Glu Arg Leu Glu Phe Gly Ser Leu Leu His Glu Phe Gly Leu Leu Glu
                    355                 360                 365

Ala Pro Ala Pro Leu Glu Glu Ala Pro Trp Pro Pro Glu Gly Ala
                370                 375                 380

Phe Val Gly Phe Val Leu Ser Arg Pro Glu Pro Met Trp Ala Glu Leu
            385                 390                 395                 400

Lys Ala Leu Ala Ala Cys Arg Asp Gly Arg Val His Arg Ala Ala Asp
                            405                 410                 415

Pro Leu Ala Gly Leu Lys Asp Leu Lys Glu Val Arg Gly Leu Leu Ala
                        420                 425                 430

Lys Asp Leu Ala Val Leu Ala Ser Arg Glu Gly Leu Asp Leu Val Pro
            435                 440                 445

Gly Asp Asp Pro Met Leu Leu Ala Tyr Leu Leu Asp Pro Ser Asn Thr
                            450                 455                 460

Thr Pro Glu Gly Val Ala Arg Arg Tyr Gly Gly Glu Trp Thr Glu Asp
            465                 470                 475                 480

Ala Ala His Arg Ala Leu Leu Ser Glu Arg Leu His Arg Asn Leu Leu
                        485                 490                 495
```

-continued

```
Lys Arg Leu Glu Gly Glu Lys Leu Leu Trp Leu Tyr His Glu Val
                500                 505                 510
Glu Lys Pro Leu Ser Arg Val Leu Ala His Met Glu Thr Gly Val
        515                 520                 525
Arg Leu Asp Val Ala Tyr Leu Gln Ala Leu Ser Leu Glu Leu Ala Glu
    530                 535                 540
Glu Ile Arg Arg Leu Glu Glu Val Phe Arg Leu Ala Gly His Pro
545                 550                 555                 560
Phe Asn Leu Asn Ser Arg Asp Gln Leu Glu Arg Val Leu Phe Asp Glu
                565                 570                 575
Leu Arg Leu Pro Ala Leu Gly Lys Thr Gln Lys Thr Gly Lys Arg Ser
        580                 585                 590
Thr Ser Ala Ala Val Leu Glu Ala Leu Arg Glu Ala His Pro Ile Val
    595                 600                 605
Glu Lys Ile Leu Gln His Arg Glu Leu Thr Lys Leu Lys Asn Thr Tyr
    610                 615                 620
Val Asp Pro Leu Pro Ser Leu Val His Pro Arg Thr Gly Arg Leu His
625                 630                 635                 640
Thr Arg Phe Asn Gln Thr Ala Thr Ala Thr Gly Arg Leu Ser Ser Ser
                645                 650                 655
Asp Pro Asn Leu Gln Asn Ile Pro Val Arg Thr Pro Leu Gly Gln Arg
            660                 665                 670
Ile Arg Arg Ala Phe Val Ala Glu Ala Gly Trp Ala Leu Val Ala Leu
        675                 680                 685
Asp Tyr Ser Gln Ile Glu Leu Arg Val Leu Ala His Leu Ser Gly Asp
    690                 695                 700
Glu Asn Leu Ile Arg Val Phe Gln Glu Gly Lys Asp Ile His Thr Gln
705                 710                 715                 720
Thr Ala Ser Trp Met Phe Gly Val Pro Pro Glu Ala Val Asp Pro Leu
                725                 730                 735
Met Arg Arg Ala Ala Lys Thr Val Asn Phe Gly Val Leu Tyr Gly Met
            740                 745                 750
Ser Ala His Arg Leu Ser Gln Glu Leu Ala Ile Pro Tyr Glu Glu Ala
        755                 760                 765
Val Ala Phe Ile Glu Arg Tyr Phe Gln Ser Phe Pro Lys Val Arg Ala
    770                 775                 780
Trp Ile Glu Lys Thr Leu Glu Glu Gly Arg Lys Arg Gly Tyr Val Glu
785                 790                 795                 800
Thr Leu Phe Gly Arg Arg Tyr Val Pro Asp Leu Asn Ala Arg Val
                805                 810                 815
Lys Ser Val Arg Glu Ala Ala Glu Arg Met Ala Phe Asn Met Pro Val
            820                 825                 830
Gln Gly Thr Ala Ala Asp Leu Met Lys Leu Ala Met Val Lys Leu Phe
        835                 840                 845
Pro Arg Leu Arg Glu Met Gly Ala Arg Met Leu Leu Gln Val His Asp
    850                 855                 860
Glu Leu Leu Leu Glu Ala Pro Gln Ala Arg Ala Glu Glu Val Ala Ala
865                 870                 875                 880
Leu Ala Lys Glu Ala Met Glu Lys Ala Tyr Pro Leu Ala Val Pro Leu
                885                 890                 895
Glu Val Glu Val Gly Met Gly Glu Asp Trp Leu Ser Ala Lys Gly
            900                 905                 910
```

<210> SEQ ID NO 12
<211> LENGTH: 20
<212> TYPE: DNA
<213> ORGANISM: Artificial Sequence
<220> FEATURE:
<223> OTHER INFORMATION: PCR forward Primer COG1F
<220> FEATURE:
<221> NAME/KEY: misc_feature
<222> LOCATION: (12)..(12)
<223> OTHER INFORMATION: n is a, c, g, or t

<400> SEQUENCE: 12
cgytggatgc gnttycatga                                           20

<210> SEQ ID NO 13
<211> LENGTH: 22
<212> TYPE: DNA
<213> ORGANISM: Artificial Sequence
<220> FEATURE:
<223> OTHER INFORMATION: PCR Reverse Primer COG1R

<400> SEQUENCE: 13
cttagacgcc atcatcatty ac                                        22

<210> SEQ ID NO 14
<211> LENGTH: 26
<212> TYPE: DNA
<213> ORGANISM: Artificial Sequence
<220> FEATURE:
<223> OTHER INFORMATION: PCR forward Primer COG2F
<220> FEATURE:
<221> NAME/KEY: misc_feature
<222> LOCATION: (9)..(9)
<223> OTHER INFORMATION: n is a, c, g, or t

<400> SEQUENCE: 14
cargarbcna tgttyagrtg gatgag                                    26

<210> SEQ ID NO 15
<211> LENGTH: 21
<212> TYPE: DNA
<213> ORGANISM: Artificial Sequence
<220> FEATURE:
<223> OTHER INFORMATION: PCR Reverse Primer COG2R

<400> SEQUENCE: 15
tcgacgccat cttcattcac a                                         21

<210> SEQ ID NO 16
<211> LENGTH: 20
<212> TYPE: DNA
<213> ORGANISM: Artificial Sequence
<220> FEATURE:
<223> OTHER INFORMATION: Probe RING1-TP(a). 5'-end is labeled Cy5 and
    3'-end is labeled BHQ3

<400> SEQUENCE: 16
agatygcgat cycctgtcca                                           20

<210> SEQ ID NO 17
<211> LENGTH: 20
<212> TYPE: DNA
<213> ORGANISM: Artificial Sequence
<220> FEATURE:
<223> OTHER INFORMATION: Probe RING2AL-TP. 5'end is labeled ROX and
    3'-end is labeled BHQ2

<400> SEQUENCE: 17
tgggagggsg atcgcratct                                                  20

<210> SEQ ID NO 18
<211> LENGTH: 12
<212> TYPE: PRT
<213> ORGANISM: Artificial Sequence
<220> FEATURE:
<223> OTHER INFORMATION: A partial sequence (A1-A12) of Tth DNA
      polymerase

<400> SEQUENCE: 18

Leu Ser Gln Glu Leu Ala Ile Pro Tyr Glu Glu Ala
1               5                   10

<210> SEQ ID NO 19
<211> LENGTH: 12
<212> TYPE: PRT
<213> ORGANISM: Artificial Sequence
<220> FEATURE:
<223> OTHER INFORMATION: A partial sequence (A1-A12) of Tth DNA
      polymerase variant

<400> SEQUENCE: 19

Leu Ser Arg Glu Leu Ala Ile Pro Tyr Arg Glu Ala
1               5                   10

<210> SEQ ID NO 20
<211> LENGTH: 12
<212> TYPE: PRT
<213> ORGANISM: Artificial Sequence
<220> FEATURE:
<223> OTHER INFORMATION: A partial sequence (A1-A12) of Bca polymerase

<400> SEQUENCE: 20

Leu Ala Gln Asn Leu Asn Ile Ser Arg Lys Glu Ala
1               5                   10

<210> SEQ ID NO 21
<211> LENGTH: 12
<212> TYPE: PRT
<213> ORGANISM: Artificial Sequence
<220> FEATURE:
<223> OTHER INFORMATION: A partial sequence (A1-A12) of Bst polymerase

<400> SEQUENCE: 21

Leu Ala Gln Asn Leu Asn Ile Thr Arg Lys Glu Ala
1               5                   10

<210> SEQ ID NO 22
<211> LENGTH: 12
<212> TYPE: PRT
<213> ORGANISM: Artificial Sequence
<220> FEATURE:
<223> OTHER INFORMATION: A partial sequence (A1-A12) of Aac polymerase

<400> SEQUENCE: 22

Leu Ala Gln Asn Leu Asn Ile Pro Gln Lys Glu Ala
1               5                   10

<210> SEQ ID NO 23
<211> LENGTH: 592
<212> TYPE: PRT
<213> ORGANISM: Artificial Sequence
<220> FEATURE:
<223> OTHER INFORMATION: DNA polymerase I Bacillus caldotenax

<400> SEQUENCE: 23

```
Met Glu Ser Pro Ser Ser Glu Glu Lys Pro Leu Ala Lys Met Ala
1               5                   10                  15

Phe Thr Leu Ala Asp Arg Val Thr Glu Met Leu Ala Asp Lys Ala
                20                  25                  30

Ala Leu Val Val Glu Val Val Glu Glu Asn Tyr His Asp Ala Pro Ile
            35                  40                  45

Val Gly Ile Ala Val Val Asn Glu His Gly Arg Phe Phe Leu Arg Pro
50                  55                  60

Glu Thr Ala Leu Ala Asp Pro Gln Phe Val Ala Trp Leu Gly Asp Glu
65                  70                  75                  80

Thr Lys Lys Lys Ser Met Phe Asp Ser Lys Arg Ala Ala Val Ala Leu
                85                  90                  95

Lys Trp Lys Gly Ile Glu Leu Cys Gly Val Ser Phe Asp Leu Leu Leu
                100                 105                 110

Ala Ala Tyr Leu Leu Asp Pro Ala Gln Gly Val Asp Asp Val Ala Ala
            115                 120                 125

Ala Ala Lys Met Lys Gln Tyr Glu Ala Val Arg Pro Asp Glu Ala Val
            130                 135                 140

Tyr Gly Lys Gly Ala Lys Arg Ala Val Pro Asp Glu Pro Val Leu Ala
145                 150                 155                 160

Glu His Leu Val Arg Lys Ala Ala Ile Trp Ala Leu Glu Arg Pro
                165                 170                 175

Phe Leu Asp Glu Leu Arg Arg Asn Glu Gln Asp Arg Leu Leu Val Glu
                180                 185                 190

Leu Glu Gln Pro Leu Ser Ser Ile Leu Ala Glu Met Glu Phe Ala Gly
                195                 200                 205

Val Lys Val Asp Thr Lys Arg Leu Glu Gln Met Gly Glu Glu Leu Ala
            210                 215                 220

Glu Gln Leu Arg Thr Val Glu Gln Arg Ile Tyr Glu Leu Ala Gly Gln
225                 230                 235                 240

Glu Phe Asn Ile Asn Ser Pro Lys Gln Leu Gly Val Ile Leu Phe Glu
                245                 250                 255

Lys Leu Gln Leu Pro Val Leu Lys Lys Thr Lys Thr Gly Tyr Ser Thr
            260                 265                 270

Ser Ala Asp Val Leu Glu Lys Leu Ala Pro Tyr His Glu Ile Val Glu
            275                 280                 285

Asn Ile Leu His Tyr Arg Gln Leu Gly Lys Leu Gln Ser Thr Tyr Ile
            290                 295                 300

Glu Gly Leu Leu Lys Val Val Arg Pro Asp Thr Lys Lys Val His Thr
305                 310                 315                 320

Ile Phe Asn Gln Ala Leu Thr Gln Thr Gly Arg Leu Ser Ser Thr Glu
                325                 330                 335

Pro Asn Leu Gln Asn Ile Pro Ile Arg Leu Glu Glu Gly Arg Lys Ile
            340                 345                 350

Arg Gln Ala Phe Val Pro Ser Glu Ser Asp Trp Leu Ile Phe Ala Ala
            355                 360                 365

Asp Tyr Ser Gln Ile Glu Leu Arg Val Leu Ala His Ile Ala Glu Asp
            370                 375                 380

Asp Asn Leu Met Glu Ala Phe Arg Arg Asp Leu Asp Ile His Thr Lys
385                 390                 395                 400

Thr Ala Met Asp Ile Phe Gln Val Ser Glu Asp Glu Val Thr Pro Asn
                405                 410                 415
```

```
Met Arg Arg Gln Ala Lys Ala Val Asn Phe Gly Ile Val Tyr Gly Ile
                420                 425                 430

Ser Asp Tyr Gly Leu Ala Gln Asn Leu Asn Ile Ser Arg Lys Glu Ala
            435                 440                 445

Ala Glu Phe Ile Glu Arg Tyr Phe Glu Ser Phe Pro Gly Val Lys Arg
        450                 455                 460

Tyr Met Glu Asn Ile Val Gln Glu Ala Lys Gln Lys Gly Tyr Val Thr
465                 470                 475                 480

Thr Leu Leu His Arg Arg Arg Tyr Leu Pro Asp Ile Thr Ser Arg Asn
                485                 490                 495

Phe Asn Val Arg Ser Phe Ala Glu Arg Met Ala Met Asn Thr Pro Ile
            500                 505                 510

Gln Gly Ser Ala Ala Asp Ile Ile Lys Lys Ala Met Ile Asp Leu Asn
        515                 520                 525

Ala Arg Leu Lys Glu Glu Arg Leu Gln Ala Arg Leu Leu Leu Gln Val
530                 535                 540

His Asp Glu Leu Ile Leu Glu Ala Pro Lys Glu Met Glu Arg Leu
545                 550                 555                 560

Cys Arg Leu Val Pro Glu Val Met Glu Gln Ala Val Thr Leu Arg Val
                565                 570                 575

Pro Leu Lys Val Asp Tyr His Tyr Gly Ser Thr Trp Tyr Asp Ala Lys
            580                 585                 590

<210> SEQ ID NO 24
<211> LENGTH: 609
<212> TYPE: PRT
<213> ORGANISM: Artificial Sequence
<220> FEATURE:
<223> OTHER INFORMATION: DNA polymerase I Alicyclobacillus
      acidocaldarius

<400> SEQUENCE: 24

Met Glu Leu Asp Phe Arg Ser Leu Val Asp Lys Ile Ser Glu Glu Met
1               5                   10                  15

Ser His Asp Ser Thr Pro Thr Pro Ser Pro Ala Ala Ala Ser Gly Ala
                20                  25                  30

Ser Ser Glu Trp Ser Ser Phe Ala Tyr Gly Leu Ile Glu Asp Ala Gly
            35                  40                  45

Ala Trp Gln Glu Ala Ile Ser Ser Phe Ser Glu Pro Val Gly Val Met
        50                  55                  60

Met Asp Leu Ala Asp Pro Asp Tyr His Arg Ala Glu Ile Arg Gly Met
65                  70                  75                  80

Ala Val Ala Thr Pro Lys Arg Ala Tyr Tyr Val Arg Phe Gly Glu Arg
                85                  90                  95

Leu Glu Leu Ser Asp Val Arg Pro Trp Leu Val Ser Asp Arg Pro Lys
            100                 105                 110

Val Ala Phe Asp Leu Lys Ser Met Ala Phe Ala Leu Asp Ala His Gly
        115                 120                 125

Ile Gly Leu Thr Ser Glu Cys Gly Trp Gln Asp Val Lys Leu Ala Ala
130                 135                 140

Tyr Leu Leu Asn Pro Gln Asp Gly Glu Val Glu Leu Ser Asp Val Phe
145                 150                 155                 160

Ala Arg Glu Arg Gly Gln Glu Leu Pro Ala Trp Glu Glu Gly Glu Arg
                165                 170                 175

Glu Lys Trp Leu Ala Tyr Thr Ala Ser Gln Leu Pro Pro Leu Phe Glu
            180                 185                 190
```

Ser Leu Ala Tyr Thr Ile Arg Met Gln Glu Met Glu Arg Leu Tyr Gln
    195                 200                 205

Glu Val Glu Leu Pro Leu Ala Phe Val Leu Ala Lys Met Glu Ile Thr
210                 215                 220

Gly Phe Tyr Val Asn Arg Glu Lys Leu Val Ala Phe Gly Gln Glu Leu
225                 230                 235                 240

Thr Glu Arg Ile Lys Arg Ile Thr Gln Glu Ile Tyr Asp Leu Ala Gly
                245                 250                 255

Thr Ser Phe Asn Leu Asn Ser Pro Lys Gln Leu Gly Glu Ile Leu Phe
            260                 265                 270

Asp Lys Leu Gly Leu Pro Ala Leu Lys Lys Thr Lys Thr Gly Tyr Ser
        275                 280                 285

Thr Ser Ala Asp Val Leu Glu Lys Leu Ala Pro Met His Glu Ile Val
    290                 295                 300

Gln Lys Ile Leu Asp Tyr Arg Leu Leu Ala Lys Leu Gln Ser Thr Tyr
305                 310                 315                 320

Val Glu Gly Leu Leu Lys Val Ile Arg Lys Glu Thr Gly Arg Val His
                325                 330                 335

Thr Arg Phe His Gln Thr Leu Thr Ala Thr Gly Arg Leu Ser Ser Ser
            340                 345                 350

Glu Pro Asn Leu Gln Asn Ile Pro Ile Arg Leu Glu Glu Gly Arg Arg
        355                 360                 365

Leu Arg Gln Val Phe Glu Pro Thr Tyr Lys Asp Trp Val Ile Phe Ala
    370                 375                 380

Ala Asp Tyr Ser Gln Ile Glu Leu Arg Ile Leu Ala His Leu Ser Gly
385                 390                 395                 400

Asp Glu Ala Leu Ile Asp Ala Phe Arg Arg Asp Met Asp Ile His Thr
                405                 410                 415

Arg Thr Ala Ala Asp Val Phe Glu Val Pro Pro Glu Gln Val Thr Ser
            420                 425                 430

Leu Met Arg Arg Gln Ala Lys Ala Val Asn Phe Gly Ile Val Tyr Gly
        435                 440                 445

Ile Ser Asp Phe Gly Leu Ala Gln Asn Leu Asn Ile Pro Gln Lys Glu
    450                 455                 460

Ala Lys Arg Phe Ile Glu Ser Tyr Phe Glu Lys Phe Pro Gly Val Lys
465                 470                 475                 480

Arg Tyr Met Asp Glu Ile Val Lys Gln Ala Arg Glu Arg Gly Tyr Val
                485                 490                 495

Thr Thr Leu Met Asn Arg Arg Arg Tyr Leu Pro Asp Ile His Ser Arg
            500                 505                 510

Asn Tyr Gln Leu Arg Ser Phe Ala Glu Arg Thr Ala Met Asn Thr Pro
        515                 520                 525

Ile Gln Gly Ser Ala Ala Asp Leu Ile Lys Leu Ala Met Val Arg Ile
    530                 535                 540

Asp Arg Ala Met Arg Asp Ala Gln Met Asp Ala Arg Met Leu Leu Gln
545                 550                 555                 560

Val His Asp Glu Leu Ile Phe Glu Cys Pro Lys Asp Glu Leu Ala Ala
                565                 570                 575

Leu Glu Val Leu Val Arg Asp Asn Met Glu Asn Ala Met Thr Leu Ser
            580                 585                 590

Val Pro Leu Lys Val Asp Thr Ala Tyr Gly Pro Thr Trp Tyr Asp Ala
        595                 600                 605

Lys

<210> SEQ ID NO 25
<211> LENGTH: 832
<212> TYPE: PRT
<213> ORGANISM: Artificial Sequence
<220> FEATURE:
<223> OTHER INFORMATION: DNA polymerase I Thermus aquaticus

<400> SEQUENCE: 25

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Ala Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
```

```
                355                 360                 365
Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
            450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
            770                 775                 780
```

```
Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
            805                 810                 815

Leu Glu Val Glu Val Gly Ile Gly Glu Asp Trp Leu Ser Ala Lys Glu
        820                 825                 830

<210> SEQ ID NO 26
<211> LENGTH: 19
<212> TYPE: DNA
<213> ORGANISM: Artificial Sequence
<220> FEATURE:
<223> OTHER INFORMATION: PCR forward Primer hACTB-F

<400> SEQUENCE: 26
tggcacccag cacaatgaa                                                  19

<210> SEQ ID NO 27
<211> LENGTH: 20
<212> TYPE: DNA
<213> ORGANISM: Artificial Sequence
<220> FEATURE:
<223> OTHER INFORMATION: PCR Reverse Primer hACTB-533

<400> SEQUENCE: 27
atcacctccc ctgtgtggac                                                 20

<210> SEQ ID NO 28
<211> LENGTH: 954
<212> TYPE: PRT
<213> ORGANISM: Geobacillus stearothermophilus

<400> SEQUENCE: 28

Met Ala Ser Thr Arg Arg Ala Ala Thr Gln Ala Gly Arg Ala Gly
1               5                   10                  15

Pro Phe Asp Arg Gln Ala Leu Gly Arg Gly Ala Ser Arg Leu His Tyr
            20                  25                  30

Gly Asp Glu Arg Ser Arg Ala Arg His Arg Val Tyr Asp Ser Phe Pro
        35                  40                  45

Glu Ala Gly Ala Val Ala Gly Phe Phe Leu Trp Pro Pro Ala Trp
    50                  55                  60

Tyr Asn Arg Thr Arg Asn Val Arg Gly Gly Met Met Leu Lys Asn Lys
65                  70                  75                  80

Leu Val Leu Ile Asp Gly Asn Ser Val Ala Tyr Arg Ala Phe Phe Ala
                85                  90                  95

Leu Pro Leu Leu His Asn Asp Lys Gly Ile His Thr Asn Ala Val Tyr
            100                 105                 110

Gly Phe Thr Met Met Leu Asn Lys Ile Leu Ala Glu Glu Gln Pro Thr
        115                 120                 125

His Ile Leu Val Ala Phe Asp Ala Gly Lys Thr Thr Phe Arg His Glu
    130                 135                 140

Thr Phe Gln Asp Tyr Lys Gly Gly Arg Gln Gln Thr Pro Pro Glu Leu
145                 150                 155                 160

Ser Glu Gln Phe Pro Leu Val Arg Glu Leu Lys Ala Tyr Arg Ile
                165                 170                 175

Pro Ala Tyr Glu Leu Asp His Tyr Glu Ala Asp Asp Ile Ile Gly Thr
            180                 185                 190

Met Ala Ala Arg Ala Glu Arg Glu Gly Phe Ala Val Lys Val Ile Ser
```

```
            195                 200                 205
Gly Asp Arg Asp Leu Thr Gln Leu Ala Ser Pro Gln Val Thr Val Glu
210                 215                 220
Ile Thr Lys Lys Gly Ile Thr Asp Ile Glu Ser Tyr Thr Pro Glu Thr
225                 230                 235                 240
Val Val Glu Lys Tyr Gly Leu Thr Pro Glu Gln Ile Val Asp Leu Lys
            245                 250                 255
Gly Leu Met Gly Asp Lys Ser Asp Asn Ile Pro Gly Val Pro Gly Ile
            260                 265                 270
Gly Lys Lys Thr Ala Val Lys Leu Leu Lys Gln Phe Gly Thr Val Glu
            275                 280                 285
Asn Val Leu Ala Ser Ile Asp Glu Ile Lys Gly Glu Lys Leu Lys Glu
290                 295                 300
Asn Leu Arg Gln Tyr Arg Asp Leu Ala Leu Leu Ser Lys Gln Leu Ala
305                 310                 315                 320
Ala Ile Cys Arg Asp Ala Pro Val Glu Leu Thr Leu Asp Asp Ile Val
            325                 330                 335
Tyr Lys Gly Glu Asp Arg Glu Lys Val Val Ala Leu Phe Gln Glu Leu
            340                 345                 350
Gly Phe Gln Ser Phe Leu Asp Lys Met Ala Val Gln Thr Asp Glu Gly
            355                 360                 365
Glu Lys Pro Leu Ala Gly Met Asp Phe Ala Ile Ala Asp Ser Val Thr
370                 375                 380
Asp Glu Met Leu Ala Asp Lys Ala Ala Leu Val Val Glu Val Val Gly
385                 390                 395                 400
Asp Asn Tyr His His Ala Pro Ile Val Gly Ile Ala Leu Ala Asn Glu
            405                 410                 415
Arg Gly Arg Phe Phe Leu Arg Pro Glu Thr Ala Val Ala Asp Pro Lys
            420                 425                 430
Phe Leu Ala Trp Leu Gly Asp Glu Thr Lys Lys Lys Thr Met Phe Asp
            435                 440                 445
Ser Lys Arg Ala Ala Val Ala Leu Asn Gly Lys Gly Ile Glu Leu Ala
450                 455                 460
Gly Val Gly Val Val Phe Asp Leu Leu Leu Ala Ala Tyr Leu Leu Asp
465                 470                 475                 480
Pro Ala Gln Ala Ala Gly Asp Val Ala Ala Val Ala Lys Met His Gln
            485                 490                 495
Tyr Glu Ala Val Arg Ser Asp Glu Ala Val Tyr Gly Lys Gly Ala Lys
            500                 505                 510
Arg Thr Val Pro Asp Glu Pro Thr Leu Ala Glu Gln Leu Val Arg Lys
            515                 520                 525
Ala Ala Ile Trp Ala Leu Glu Glu Pro Leu Met Asp Glu Leu Arg
            530                 535                 540
Arg Asn Glu Gln Asp Arg Leu Leu Thr Glu Leu Glu His Ala Leu Ala
545                 550                 555                 560
Gly Ile Leu Ala Asn Met Glu Phe Thr Gly Val Lys Val Asp Thr Lys
            565                 570                 575
Arg Leu Glu Gln Met Gly Ala Glu Leu Thr Glu Gln Leu Gln Ala Val
            580                 585                 590
Glu Arg Arg Ile Tyr Glu Leu Ala Gly Gln Glu Phe Asn Ile Asn Ser
            595                 600                 605
Pro Lys Gln Leu Gly Thr Val Leu Phe Asp Lys Leu Gln Leu Pro Val
            610                 615                 620
```

```
Leu Lys Lys Thr Lys Thr Gly Tyr Ser Thr Ser Ala Asp Val Leu Glu
625             630                 635                 640

Lys Leu Ala Pro His His Glu Ile Val Glu His Ile Leu His Tyr Arg
            645                 650                 655

Gln Leu Gly Lys Leu Gln Ser Thr Tyr Ile Glu Gly Leu Leu Lys Val
            660                 665                 670

Val His Pro Val Thr Gly Lys Val His Thr Met Phe Asn Gln Ala Leu
            675                 680                 685

Thr Gln Thr Gly Arg Leu Ser Ser Val Glu Pro Asn Leu Gln Asn Ile
690                 695                 700

Pro Ile Arg Leu Glu Glu Gly Arg Lys Ile Arg Gln Ala Phe Val Pro
705                 710                 715                 720

Ser Glu Pro Asp Trp Leu Ile Phe Ala Ala Asp Tyr Ser Gln Ile Glu
                725                 730                 735

Leu Arg Val Leu Ala His Ile Ala Glu Asp Asp Asn Leu Ile Glu Ala
                740                 745                 750

Phe Arg Arg Trp Leu Asp Ile His Thr Lys Thr Ala Met Asp Ile Phe
            755                 760                 765

His Val Ser Glu Glu Asp Val Thr Ala Asn Met Arg Arg Gln Ala Lys
    770                 775                 780

Ala Val Asn Phe Gly Ile Val Tyr Gly Ile Ser Asp Tyr Gly Leu Ala
785                 790                 795                 800

Gln Asn Leu Asn Ile Thr Arg Lys Glu Ala Ala Glu Phe Ile Glu Arg
                805                 810                 815

Tyr Phe Ala Ser Phe Pro Gly Val Lys Gln Tyr Met Asp Asn Ile Val
            820                 825                 830

Gln Glu Ala Lys Gln Lys Gly Tyr Val Thr Thr Leu Leu His Arg Arg
            835                 840                 845

Arg Tyr Leu Pro Asp Ile Thr Ser Arg Asn Phe Asn Val Arg Thr Phe
850                 855                 860

Ala Glu Arg Thr Ala Met Asn Thr Pro Ile Gln Gly Ser Ala Ala Asp
865                 870                 875                 880

Ile Ile Lys Lys Ala Met Ile Asp Leu Ser Val Ser Val Arg Glu Glu
            885                 890                 895

Arg Leu Gln Ala Arg Leu Leu Leu Gln Gly His Asp Glu Leu Ile Leu
            900                 905                 910

Glu Ala Pro Lys Glu Glu Ile Gly Arg Leu Cys Arg Leu Val Pro Glu
            915                 920                 925

Val Met Glu Gln Ala Val Thr Leu Arg Val Pro Leu Lys Val Asp Tyr
            930                 935                 940

His Tyr Gly Pro Thr Trp Tyr Asp Ala Lys
945                 950
```

DNA POLYMERASE MUTANT SUITED TO NUCLEIC ACID AMPLIFICATION FROM RNA

A sequence listing in electronic (ASCII text file) format is filed with this application and incorporated herein by reference. The name of the ASCII text file is "17-257986-revised-seq-listing-may-2022.txt"; the file was created on May 20, 2022; the size of the file is 75 KB.

TECHNICAL FIELD

The present invention relates to a DNA polymerase mutant suitable for nucleic acid amplification reaction from RNA. Furthermore, the present invention relates to a method for enhancing the activity of an existing DNA polymerase on nucleic acid amplification from RNA, and a method for producing a DNA polymerase mutant suitable for nucleic acid amplification reaction from RNA.

BACKGROUND ART

DNA polymerases play a central role in accurately transmitting genetic information from generation to generation, that is, in replication and retention of genomes. DNA polymerases function intracellularly as an enzyme responsible for DNA synthesis, and polymerize deoxyribonucleoside triphosphates in the presence of metal activators such as $Mg^{2+}$ on an order required for replication of a DNA template or a polynucleotide template. DNA polymerases are involved in a series of DNA synthesis processes including DNA replication, DNA repair, recombination and gene amplification in vivo. During the DNA synthesis processes, the DNA template is replicated once or several times to produce identical replicas. In contrast, DNA replication can be repeated many times in vitro, for example in a polymerase chain reaction.

So-called reverse transcription polymerase chain reaction (RT-PCR) is a technique for detecting or quantifying a target RNA by amplification and used in many applications. In order to amplify a target RNA by PCR, an RNA template first needs to be reverse transcribed to cDNA. A typical RT-PCR method is performed by using a reverse transcriptase for synthesizing cDNA from an RNA template and a heat-resistant DNA polymerase for performing nucleic acid amplification from the synthesized cDNA as a template. In such a case, it is necessary to select a reaction solution composition suitable for both the reverse transcriptase and the heat-resistant DNA polymerase to be used. In some cases, the lid of a reaction tube may be opened between the reverse transcription reaction and the subsequent nucleic acid amplification reaction, and the risk of cross-contamination cannot be ignored. Thus, a one-step RT-PCR method has been developed for performing a reverse transcription reaction and PCR continuously without opening a reaction vessel. In this method, a DNA polymerase having a reverse transcriptase activity may be used. However, since a reverse transcription reaction and PCR are performed using the same reaction solution composition, it is necessary to balance the reverse transcription reaction and PCR. Further, a technique for enhancing the reverse transcription efficiency when the reverse transcription reaction and PCR are performed in the same reaction solution composition has been reported. (See Patent Literatures 1 to 3).

In recent years, various isothermal nucleic acid amplification reaction methods have been proposed and put into practical use. The isothermal nucleic acid amplification methods are also often used in combination with a reverse transcription reaction using an RNA as a template, and the same problem as RT-PCR methods as described above has arisen. In other words, also for the RT-isothermal nucleic acid amplification methods, it is necessary to perform a reverse transcription reaction and isothermal nucleic acid amplification in the same reaction solution composition and balance the reverse transcription reaction and the isothermal nucleic acid amplification.

CITATION LIST

Patent Literatures

Patent Literature 1: JP-B 3844975
Patent Literature 2: WO2012/139748
Patent Literature 3: WO2014/090836

SUMMARY OF INVENTION

Problem to be Solved by the Invention

An object of the present invention to provide a genetic engineering improvement method for creating a DNA polymerase having a reverse transcriptase activity which is suitable for performing a reverse transcription reaction and a nucleic acid amplification reaction in the same container.

Solution for Problem

The present inventors diligently studied to develop a DNA polymerase mutant having a reverse transcriptase activity which is suitable for performing a reverse transcription reaction and a nucleic acid amplification reaction. As a result, the present inventors surprisingly succeeded in finding a method of producing a DNA polymerase mutant having a reverse transcriptase activity that is superior to conventional techniques by introducing a mutation into a specific position in an amino acid sequence. Thus the present invention was completed.

The first embodiment of the present invention relates to a mutant of a DNA polymerase having a reverse transcriptase activity and comprising a sequence consisting of 12 amino acids A1-A12:

A1 is a branched chain amino acid residue,
A2 is a hydrophilic neutral amino acid residue or a hydrophobic aliphatic amino acid residue,
A3 is a hydrophilic neutral amino acid residue,
A4 is an acidic amino acid residue or a hydrophilic neutral amino acid residue,
A5 is a branched chain amino acid residue,
A6 is a hydrophobic aliphatic amino acid residue or a hydrophilic neutral amino acid residue,
A7 is a branched chain amino acid residue,
A8 is a proline residue or a hydrophilic neutral amino acid residue,
A9 is a hydrophobic aromatic amino acid residue, a basic amino acid residue, or a hydrophilic neutral amino acid residue,
A10 is an acidic amino acid residue or a basic amino acid residue,
A11 is an acidic amino acid residue, and
A12 is a hydrophobic aliphatic amino acid residue;
wherein A3 and/or A10 is replaced by a basic amino acid residue that is different from the amino acid residue before introduction of mutation.

In the DNA polymerase mutant having a reverse transcriptase activity of the first embodiment of the present invention, the sequence consisting of 12 amino acids before introduction of mutation preferably comprises leucine as A1, glutamine as A3, leucine as A5, isoleucine as A7, glutamic acid as A11 and alanine as A12. In the DNA polymerase mutant having a reverse transcriptase activity of the first embodiment of the present invention, A3 and/or A10 in the sequence consisting of 12 amino acids is preferably replaced by an amino acid selected from the group consisting of lysine, arginine and histidine. For example, it is preferable that A3 and/or A10 is replaced by arginine.

The DNA polymerase mutant having a reverse transcriptase activity of the first embodiment of the present invention may be derived from any DNA polymerase that is not particularly limited, as long as the mutant is derived from a DNA polymerase having a reverse transcriptase activity that is suitable for performing a reverse transcription reaction and a nucleic acid amplification reaction in the same container. For example, the DNA polymerase mutant of the present invention is preferably derived from a DNA polymerase from *Thermus thermophilus*, a DNA polymerase from *Thermus aquaticus*, a DNA polymerase from *Bacillus cardotenax*, a DNA polymerase from *Bacillus stearothermophilus*, or a DNA polymerase from *Alicyclobacillus acidocaldarius*.

The second embodiment of the present invention relates to a kit containing the DNA polymerase mutant having a reverse transcriptase activity of the first embodiment of the present invention. The kit may contain various components as a kit for preparing a reaction solution suitable for a reverse transcription reaction and a nucleic acid amplification reaction as described later.

The third embodiment of the present invention relates to a composition comprising the DNA polymerase mutant having a reverse transcriptase activity of the first embodiment of the present invention. The composition may comprise various components as a composition suitable for a reverse transcription reaction and a nucleic acid amplification reaction as described later.

The fourth embodiment of the present invention relates to a method for producing a DNA polymerase having a reverse transcriptase activity suitable for nucleic acid amplification from an RNA, the method comprising:

(1) a step of selecting a DNA polymerase comprising a sequence consisting of 12 amino acids A1-A12:
  A1 is a branched chain amino acid residue,
  A2 is a hydrophilic neutral amino acid residue or a hydrophobic aliphatic amino acid residue,
  A3 is a hydrophilic neutral amino acid residue,
  A4 is an acidic amino acid residue or a hydrophilic neutral amino acid residue,
  A5 is a branched chain amino acid residue,
  A6 is a hydrophobic aliphatic amino acid residue or a hydrophilic neutral amino acid residue,
  A7 is a branched chain amino acid residue,
  A8 is a proline residue or a hydrophilic neutral amino acid residue,
  A9 is a hydrophobic aromatic amino acid residue, a basic amino acid residue, or a hydrophilic neutral amino acid residue,
  A10 is an acidic amino acid residue or a basic amino acid residue,
  A11 is an acidic amino acid residue, and
  A12 is a hydrophobic aliphatic amino acid residue; and
(2) a step of replacing A3 and/or A10 in the sequence consisting of 12 amino acids of the DNA polymerase selected in step (1) by a basic amino acid residue that is different from the amino acid residue before introduction of mutation.

In the production method of the fourth embodiment of the present invention, the DNA polymerase selected in step (1) may comprise the sequence consisting of 12 amino acids in which A1 is leucine, A3 is glutamine, A5 is leucine, A7 is isoleucine, A11 is glutamic acid and A12 is alanine. In step (2), A3 and/or A10 may be replaced by an amino acid selected from the group consisting of lysine, arginine and histidine.

The production method of the fourth embodiment of the present invention may be combined with a method comprising producing a nucleic acid encoding the mutant and then introducing the nucleic acid into an appropriate host to express the mutant.

The fifth embodiment of the present invention relates to a method for improving a DNA polymerase having a reverse transcriptase activity and comprising a sequence consisting of 12 amino acids A1-A12:
  A1 is a branched chain amino acid residue,
  A2 is a hydrophilic neutral amino acid residue or a hydrophobic aliphatic amino acid residue,
  A3 is a hydrophilic neutral amino acid residue,
  A4 is an acidic amino acid residue or a hydrophilic neutral amino acid residue,
  A5 is a branched chain amino acid residue,
  A6 is a hydrophobic aliphatic amino acid residue or a hydrophilic neutral amino acid residue,
  A7 is a branched chain amino acid residue,
  A8 is a proline residue or a hydrophilic neutral amino acid residue,
  A9 is a hydrophobic aromatic amino acid residue, a basic amino acid residue, or a hydrophilic neutral amino acid residue,
  A10 is an acidic amino acid residue or a basic amino acid residue,
  A11 is an acidic amino acid residue, and
  A12 is a hydrophobic aliphatic amino acid residue; the method comprising replacing A3 and/or A10 by another basic amino acid residue.

In the improvement method of the fifth embodiment of the present invention, as the DNA polymerase having a reverse transcriptase activity, for example, a DNA polymerase comprising the sequence consisting of 12 amino acids in which A1 is leucine, A3 is glutamine, A5 is leucine, A7 is isoleucine, A11 is glutamic acid and A12 are alanine can be selected. Further, in the improvement method of the fifth embodiment of the present invention, A3 and/or A10 in the sequence consisting of 12 amino acids may be replaced, for example, by an amino acid selected from the group consisting of lysine, arginine and histidine.

In the first to fifth embodiments of the present invention, it is preferable that the DNA polymerase having a reverse transcriptase activity comprises a sequence consisting of 12 amino acids A1-A12:
  A1 is leucine,
  A2 is serine or alanine,
  A3 is glutamine,
  A4 is glutamic acid or asparagine,
  A5 is leucine,
  A6 is alanine or asparagine,
  A7 is isoleucine,
  A8 is proline, serine or threonine,
  A9 is tyrosine, arginine or glutamine,
  A10 is glutamic acid or lysine,
  A11 is glutamic acid, and A12 is alanine; and in the mutant, A3 and/or A10 is replaced by a basic amino acid residue that is different from the amino acid residue before introduction of mutation. For example, in the DNA polymerase mutant, A3 and/or A10 may be replaced by an amino acid selected from the group consisting of lysine, arginine and histidine.

Effects of the Invention

The present invention provides a DNA polymerase mutant having a reverse transcriptase activity which is suitable for performing a reverse transcription reaction and a nucleic acid amplification reaction in the same container, and a method for producing the mutant. According to the present invention, introduction of mutation as described in the present invention can be performed in any DNA polymerase having a reverse transcriptase activity and comprising a specific partial amino acid sequence shown by A1-A12 as described above. As a result, the time required for a reverse transcription reaction can be shortened as compared to conventional methods, DNA can be generated in a sufficient amount for a starting template in the subsequent nucleic acid amplification reaction, and the reverse transcriptase reaction and the nucleic acid amplification reaction can be achieved with higher detection sensitivity than conventional methods in a short time.

MODE FOR CARRYING OUT THE INVENTION

1. DNA Polymerase Mutant Having Reverse Transcriptase Activity of the Present Invention The first aspect of the present invention relates to a DNA polymerase mutant suitable for a reverse transcriptase reaction and a nucleic acid amplification reaction. The mutant of the present invention is a mutant of a DNA polymerase having a reverse transcriptase activity that comprises a sequence consisting of 12 amino acids A1-A12:
A1 is a branched chain amino acid residue;
A2 is a hydrophilic neutral amino acid residue or a hydrophobic aliphatic amino acid residue;
A3 is a hydrophilic neutral amino acid residue;
A4 is an acidic amino acid residue or a hydrophilic neutral amino acid residue;
A5 is a branched chain amino acid residue;
A6 is a hydrophobic aliphatic amino acid residue or a hydrophilic neutral amino acid residue;
A7 is a branched chain amino acid residue;
A8 is a proline residue or a hydrophilic neutral amino acid residue;
A9 is a hydrophobic aromatic amino acid residue, a basic amino acid residue, or a hydrophilic neutral amino acid residue;
A10 is an acidic amino acid residue or a basic amino acid residue;
A11 is an acidic amino acid residue; and
A12 is a hydrophobic aliphatic amino acid residue; wherein in the mutant, A3 and/or A10 is replaced by another basic amino acid residue.

The mutant comprising the constitution as described above is a DNA polymerase mutant suitable for a reverse transcription reaction and a nucleic acid amplification reaction performed in one container.

As used herein, examples of the "branched chain amino acid residue" include a valine residue, an isoleucine residue and a leucine residue. Examples of the "hydrophilic neutral amino acid residue" include a serine residue, a threonine residue, an asparagine residue and a glutamine residue.

Examples of the "hydrophobic aliphatic amino acid residue" include a glycine residue and an alanine residue. Examples of the "acidic amino acid residue" include an aspartic acid residue and a glutamic acid residue. Examples of the "hydrophobic aromatic amino acid residue" include a phenylalanine residue, a tyrosine residue and a tryptophan residue. Examples of the "basic amino acid residue" include a lysine residue, an arginine residue and a histidine residue.

In a specific aspect of the present invention, for example, a DNA polymerase having a reverse transcriptase activity and comprising the sequence consisting of 12 amino acids A1-A12 in which A1 is leucine, A3 is glutamine, A5 is leucine, A7 is isoleucine, A11 is glutamic acid and A12 is alanine can be used as a material for the mutant.

A preferred example of the mutant of the present invention is a mutant of a DNA polymerase comprising the sequences consisting of 12 amino acids A1-A12 and having a reverse transcriptase activity, wherein in the mutant, the amino acid of A3 and/or A10 is replaced by an amino acid selected from the group consisting of lysine, arginine and histidine, preferably by arginine.

A more preferred example of the mutant of the present invention is a mutant of a DNA polymerase wherein the DNA polymerase has a reverse transcriptase activity and comprises a sequence consisting of 12 amino acids A1-A12:
A1 is leucine,
A2 is serine or alanine,
A3 is glutamine,
A4 is glutamic acid or asparagine,
A5 is leucine,
A6 is alanine or asparagine,
A7 is isoleucine,
A8 is proline, serine or threonine,
A9 is tyrosine, arginine or glutamine,
A10 is glutamic acid or lysine,
A11 is glutamic acid, and
A12 is alanine;
and in the mutant, A3 and/or A10 is replaced by a basic amino acid residue that is different from the amino acid residue before introduction of mutation, for example, by an amino acid selected from the group consisting of lysine, arginine and histidine.

For example, in the case of a DNA polymerase having a reverse transcriptase activity from *Thermus thermophilus*, an amino acid sequence from positions 680 to 691 in SEQ ID NO: 1, specifically an amino acid sequence of "LSQE-LAIPYEEA" (SEQ ID NO: 18) corresponds to the sequence consisting of A1 to A12. Thus, an example of the mutant of the present invention is a mutant of the DNA polymerase from *Thermus thermophilus* in which the glutamine residue at A3 (position 682) and/or the glutamic acid residue at A10 (position 689) is replaced by an amino acid selected from the group consisting of lysine, arginine and histidine, preferably arginine. A *Thermus thermophilus*-derived DNA polymerase mutant having "LSRELAIPYREA" (SEQ ID NO: 19) can be preferably used as a DNA polymerase mutant suitable for a reverse transcriptase reaction and a nucleic acid amplification reaction. For example, mutant b13b46 which is a mutant of a DNA polymerase from *Thermus thermophilus* prepared in Example 1 has mutations Q682R and E689R as described above.

Similar mutants can be also prepared from DNA polymerases having a reverse transcriptase activity from *Thermus aquaticus, Bacillus cardotenax, Bacillus stearothermophilus*, and *Alicyclobacillus acidocaldarius*.

In a specific aspect of the present invention, for example, a DNA polymerase having a reverse transcriptase activity from *Bacillus cardotenax* has the sequence of "LAQNLNIS-RKEA" (SEQ ID NO: 20) as the sequence consisting of 12 amino acids A1-A12. Similarly, the 12-amino acid sequence of a DNA polymerase having a reverse transcriptase activity from *Bacillus stearothermophilus* is the sequence of "LAQNLNITRKEA" (SEQ ID NO: 21). Furthermore, the 12-amino acid sequence of a DNA polymerase having a reverse transcriptase activity from *Alicyclobacillus acidocaldarius* is the sequence of "LAQNLNIPQKEA" (SEQ ID NO: 22). The 12-amino acid sequence of a DNA polymerase having a reverse transcriptase activity from *Thermus aquaticus* is the sequence of "LSQELAIPYEEA" (positions 678 to 689 of SEQ ID NO: 25). When A3 and/or A10 in these amino acid sequences is replaced by a basic amino acid residue, the resulting mutants are cited as examples of the mutant of the present invention. In the mutants, for example, A3 and/or A10 is replaced by an amino acid selected from the group consisting of lysine, arginine and histidine. Particularly preferred is a mutant in which A3 and/or A10 is replaced by arginine. In addition to these mutants, examples of the DNA polymerase mutant of the present invention include mutants obtained by introducing the same mutation(s) as described above into heat-resistant polymerases from thermophilic bacteria and mesophilic DNA polymerases suitable for isothermal nucleic acid amplification methods. In other words, Pol I type or family A type DNA polymerases can also be suitably used as a target for introduction of mutation in the present invention.

The DNA polymerase mutant of the present invention may comprise the above-described mutation(s) in combination with a mutation introduced into a position other than the 12 amino acid sequence of A1-A12, as long as the reverse transcriptase activity and the nucleic acid amplification activity are not impaired. Examples of such a DNA polymerase mutant include, but not limited to, functional DNA polymerases having an amino acid sequence identity of at least 80%, 81%, 82%, 83%, 84%, 85%, 86%, 87%, 88%, 89%, 90%, 91%, 92%, 93%, 94%, 95%, 96%, 97%, 98% or 99% in a portion other than the 12 amino acid sequence of A1-A12 to the amino acid sequence of a DNA polymerase having a reverse transcriptase activity before introduction of mutation, for example a DNA polymerase having a reverse transcriptase activity from *Thermus thermophilus* (NCBI Reference Sequence WP_0112288405.1) or a DNA polymerase having a reverse transcriptase activity from *Thermus aquaticus* (Genbank Acc. No. BAA06775.1). These DNA polymerases can be suitably used in RT-PCR. Similarly, for RT-isothermal nucleic acid amplification, examples of the DNA polymerase mutant include functional DNA polymerases having an amino acid sequence identity of at least 80%, 81%, 82%, 83%, 84%, 85%, 86%, 87%, 88%, 89%, 90%, 91%, 92%, 93%, 94%, 95%, 96%, 97%, 98% or 99% in a portion other than the 12 amino acid sequence of A1-A12 to the amino acid sequence of a DNA polymerase having a reverse transcriptase activity from *Bacillus cardotenax* (NCBI Reference Sequence WP_0475858145.1), a DNA polymerase having a reverse transcriptase activity from *Bacillus stearothermophilus* (Genbank Acc. No. AAA8558.1) (SEQ ID NO: 28) or a DNA polymerase having a reverse transcriptase activity from *Alicyclobacillus acidocaldarius* (Genbank Acc. No. BAF3333.1).

The DNA polymerase mutant having a reverse transcriptase activity of the present invention may be a mutant further lacking an exonuclease activity. For example, regarding DNA polymerases from *Thermus thermophilus*, *Thermus aquaticus*, *Bacillus cardotenax*, *Bacillus stearothermophilus*, *Alicyclobacillus acidocaldarius* etc., there are known mutants lacking a 5→3 exonuclease activity. The mutants lacking the exonuclease activity lack a 5→3 exonuclease domain located at the N-terminal sides of the DNA polymerases. The mutant of the present invention may be a mutant having no 5→3 exonuclease activity in which the 5→3 exonuclease domain is deleted.

Use of the DNA polymerase mutant having a reverse transcriptase activity of the present invention results in production of a desired cDNA even under reverse transcription reaction conditions under which the DNA polymerase before introduction of mutation cannot achieve reverse transcription. Examples of the reverse transcription reaction conditions include reduced reaction time, and elevated reaction temperature. Further, use of the DNA polymerase mutant having a reverse transcriptase activity of the present invention results in an increased amount of a reverse transcription reaction product as compared to use of the DNA polymerase before introduction of mutation when reverse transcription is performed under the same conditions. For example, a reverse transcription reaction using a DNA polymerase having a reverse transcriptase activity from *Thermus thermophilus* requires a reaction time of about 30 minutes at 60° C. When the mutant of the present invention prepared from the DNA polymerase having a reverse transcriptase activity from *Thermus thermophilus* is used, the reverse transcription reaction at 60° C. can be completed in a short time of 1 to 5 minutes. In addition, the mutant of the present invention is superior in a reverse transcription reaction to a DNA polymerase mutant having a reverse transcriptase activity prepared by a technique disclosed in Japanese Patent No. 3844975. The mutant of the present invention is expected to have further improvements in terms of resistance to inhibitors during reaction and affinity with nucleic acid templates as compared to conventional DNA polymerases having a reverse transcriptase activity. According to the present invention, the reverse transcriptase activity of Pol I type or family A type DNA polymerases which originally have a low reverse transcriptase activity can be remarkably improved, and thus a DNA polymerase mutant having a reverse transcriptase activity suitable for performing a reverse transcription reaction and a nucleic acid amplification reaction can be created.

The mutant of the present invention may be a fusion protein with a PIP box (PCNA interaction protein box). PCNA, which is a protein that promotes a DNA polymerase activity, can also promote the reverse transcriptase activity of a DNA polymerase having a reverse transcriptase activity. The DNA polymerase mutant of the present invention fused with a PIP box can be prepared, for example, by using a combination of a technique as described herein and a technique as described in WO2017/090685.

2. Composition or Kit Containing the DNA Polymerase Mutant of the Present Invention The composition of the present invention means a composition comprising the DNA polymerase mutant having a reverse transcriptase activity of the present invention as described above. As an aspect of the composition of the present invention, provided is a composition suitable for a reverse transcription reaction and a nucleic acid amplification reaction which comprises the DNA polymerase mutant suitable for a reverse transcriptase reaction and a nucleic acid amplification reaction of the present invention as described in above section 1 and other components, for example components necessary for a reverse transcription reaction and a polymerase chain reaction (RT-PCR), such as a divalent metal salt, dNTPs, a buffer component, a reducing agent, sterilized water, etc. The composition of the present invention may also comprise an appropriate primer when an RNA to be amplified/detected is known. When the mutant of the present invention is suitable for a reverse transcription reaction and an isothermal nucleic acid amplification reaction, the composition of the present invention preferably comprises the same components as described above as long as the composition comprises components necessary for a reverse transcription reaction and an isothermal nucleic acid amplification reaction.

Examples of a divalent metal ion constituting the divalent metal salt include, but not limited to, a manganese ion and a magnesium ion. The divalent metal ions and their concentration suitable for reverse transcriptase are known in the art. The divalent metal ions may be supplied in the form of a salt such as chloride, sulfate or acetate. For example, the concentration of the divalent metal ion in the composition of the present invention may be preferably 0.5 to 20 mM. As the dNTP, at least one selected from the group consisting of dATP, dCTP, dGTP and dTTP, and their derivatives is used. Preferably, a mixture of dATP, dCTP, dGTP and dTTP is used.

Examples of the buffer component for maintaining pH include, but not limited to, a Tris buffer, a tricine buffer, a bicine buffer, a HEPES buffer, an acetate buffer, and a phosphate buffer. For example, the buffer components and their concentration suitable for a reverse transcription reaction and a nucleic acid amplification reaction are known in the art. Examples of the reducing agent for a reverse transcription reaction include, but not limited to, DTT (dithiothreitol) and 2-mercaptoethanol. The reducing agents and their concentration suitable for a reverse transcription reaction are known in the art.

For a reverse transcription reaction, for example, a random 6-mers oligo dT primer, and a gene-specific primer can be used as a primer. The chain length of the primer is preferably 6 nucleotides or more, more preferably 10 nucleotides or more from the viewpoint of hybridization specificity, and preferably 100 nucleotides or less, more preferably 30 nucleotides or less from the viewpoint of oligonucleotide synthesis. As a random primer for non-specific cDNA synthesis, a mixture of oligonucleotides having chain length of 6 to 8 nucleotides may be used. The oligonucleotide may be chemically synthesized, for example, by a known method, or may be derived from a biological sample. The oligonucleotide derived from a biological sample may be prepared, for example, by digesting a DNA prepared from a natural sample with a restriction endonuclease and then isolating the oligonucleotides from the digested product. For a nucleic acid amplification reaction, the composition of the present invention may comprise a pair of primers designed for a nucleic acid sequence to be amplified. The primer for a reverse transcription reaction may also serve as one of the pair of primers for a nucleic acid amplification.

The kit of the present invention is a kit for RT-PCR or a kit for RT-isothermal nucleic acid amplification which is suitable for a reverse transcription reaction method and a nucleic acid amplification reaction method. The kit of the present invention contains the DNA polymerase mutant suitable for a reverse transcription reaction and a nucleic acid amplification reaction of the present invention as described in above section 1, and a divalent metal salt, dNTPs, a buffer component, a reducing agent, or other components suitable for a reverse transcription reaction and a nucleic acid amplification reaction. Examples of the kit of the present invention include a kit for preparing a reverse transcription reaction/nucleic acid amplification reaction solution by mixing the components contained in the kit when used, a kit containing the composition of the present invention as described above which can be used only by adding a DNA template and water (sterile water etc.) to the composition when used, and a kit containing the composition of the present invention as described above in a dry form. A kit for detecting a specific RNA which contains primers specific for the target RNA and an RNA as a positive control is also included in the present invention. The divalent metal salt, the dNTPs, the buffer component and the reducing agent are as described above.

The composition and kit of the present invention may further contain a component necessary for detecting an amplified double-stranded nucleic acid, for example an intercalator or a fluorescently labeled probe. Examples of the intercalator include SYBR (registered trademark), Green I, TB Green (registered trademark), and other nucleic acid-binding dyes. Examples of the fluorescently labeled probe include TaqMan (registered trademark) probes, Cycleave (registered trademark) probes, and molecular beacon probes.

3. Method for Producing DNA Polymerase Mutant Having Reverse Transcriptase Activity of the Present Invention The method for producing a DNA polymerase mutant suitable for a reverse transcriptase reaction and a nucleic acid amplification reaction of the present invention relates to a method for producing the DNA polymerase mutant as described in above section 1.

A specific aspect of the production method of the present invention is a method for producing a DNA polymerase having a reverse transcriptase activity suitable for nucleic acid amplification from an RNA, the method comprising:

(1) a step of selecting a DNA polymerase comprising a sequence consisting of 12 amino acids A1-A12:

A1 is a branched chain amino acid residue,

A2 is a hydrophilic neutral amino acid residue or a hydrophobic aliphatic amino acid residue, A3 is a hydrophilic neutral amino acid residue, A4 is an acidic amino acid residue or a hydrophilic neutral amino acid residue, A5 is a branched chain amino acid residue, A6 is a hydrophobic aliphatic amino acid residue or a hydrophilic neutral amino acid residue, A7 is a branched chain amino acid residue, A8 is a proline residue or a hydrophilic neutral amino acid residue, A9 is a hydrophobic aromatic amino acid residue, a basic amino acid residue, or a hydrophilic neutral amino acid residue, A10 is an acidic amino acid residue or a basic amino acid residue, A11 is an acidic amino acid residue, and A12 is a hydrophobic aliphatic amino acid residue; and (2) a step of replacing A3 and/or A10 in the sequence consisting of 12 amino acids of the DNA polymerase selected in step (1) by a basic amino acid residue that is different from the amino acid residue before introduction of mutation.

In the above aspect, a DNA polymerase comprising the sequence consisting of 12 amino acids in which A1 is leucine, A3 is glutamine, A5 is leucine, A7 is isoleucine, A11 is glutamic acid and A12 is alanine may be selected as a material for introduction of mutation.

In step (2) of the production method of the present invention, A3 and/or A10 in the selected DNA polymerase having a reverse transcriptase activity is preferably replaced by is an amino acid selected from the group consisting of lysine, arginine and histidine, more preferably by arginine.

Step (1) can be performed by extracting a DNA polymerase comprising the sequence consisting of 12 amino acids A1-A12 by a conventional method, for example by computer homology search. For the search, known amino acid sequence database can be used.

Step (2) is performed by preparing a nucleic acid encoding the DNA polymerase selected in step (1), and converting codons corresponding to A3 and/or A10 in the nucleic acid into codons of basic amino acid residues. Such base substitution can be performed by a known method. For example, a commercially available kit for introduction of mutation may be used. The full length of a nucleic acid encoding the mutant into which the mutation(s) is introduced may be chemically synthesized. Furthermore, the introduction of mutation as described above may be combined with introduction of mutation into a position other than the 12 amino acid sequence of A1-A12.

For producing the DNA polymerase mutant having a reverse transcriptase activity of the present invention, a nucleic acid encoding the mutant can be prepared and introduced into an appropriate host to express the mutant. Codon optimization may be performed to allow the expression of the mutant of interest in the host used or to increase the expression level. The codon optimization is preferably performed by a method commonly used in the art.

In the production of the DNA polymerase mutant having a reverse transcriptase activity of the present invention, a nucleic acid encoding the amino acid sequence of the mutant can be inserted into an appropriate expression vector to produce the mutant. The expression vector preferably contains a nucleic acid encoding the mutant of the present invention and an expression regulatory sequence operably linked to the nucleic acid. Examples of the expression regulatory sequence include, but not limited to, a promoter, a gene involved in regulation of a promoter, a ribosome binding sequence, a polyadenylation signal, a transcription termination sequence (transcription terminator), and an enhancer. The expression vector may further contain a gene encoding a marker (drug resistance gene, fluorescence marker, luminescence marker, etc.) used for selection of a transformant.

As the expression vector into which a nucleic acid encoding the DNA polymerase mutant having a reverse transcriptase activity of the present invention is inserted, any expression vector commonly used in the art can be used. Examples of the expression vector include, but not limited to, a vector capable of self-replicating in a host cell, and a vector capable of being integrated into a host chromosome. A vector compatible with the host may be used.

Examples of the expression vector into which a nucleic acid encoding the DNA polymerase mutant having a reverse transcriptase activity of the present invention is inserted include a plasmid vector, a phage vector, and a viral vector. As the plasmid vector, a plasmid suitable for the host used can be used. For example, a plasmid derived from *Escherichia coli*, a plasmid derived from a bacterium of the genus *Bacillus*, and a plasmid derived from yeast are well known to those skilled in the art, and there are many commercially available plasmids. Such known plasmids and their mutants can be used in the present invention. As the phage vector, for example, λ phage (for example, Charon4A, Charon21A, EMBL3, EMBL4, λgt10, λgt11, λZAP) can be used. As the viral vector, for example, an animal virus such as a retrovirus or a vaccinia virus, or an insect virus such as a baculovirus can be used. Furthermore, many heterologous protein expression systems using yeast, insect cells, and mammalian cells as hosts have been constructed, and already commercially available. These expression systems may be used for the production of the DNA polymerase mutant having a reverse transcriptase activity of the present invention.

The promoter to be loaded with the expression vector used in the production method of the present invention can be selected depending on the host. When the host is *Escherichia coli*, examples of the promoter include, but not limited to, promoters derived from *Escherichia coli* and phage, such as trp promoter, lac promoter, PL promoter, and PR promoter, and their modifications. Furthermore, an expression system (for example, a pET expression system, etc.) containing a combination of a phage-derived promoter and an RNA polymerase gene may be used.

In order to facilitate purification of an expressed polypeptide, the expression vector of the present invention may further contain a nucleic acid encoding an affinity tag. A nucleic acid encoding the affinity tag is inserted into the vector so that a fusion protein of the reverse transcriptase mutant of the present invention with the affinity tag is expressed. Examples of the affinity tag include, but not limited to, a histidine (His) tag, a glutathione S-transferase (GST) tag, a maltose binding protein (MBP) tag, and a Strep (II) tag consisting of 8 amino acid residues (Trp-Ser-His-Pro-Gln-Phe-Glu-Lys). The tag may be added to the 5'-end and/or the 3'-end side of a nucleic acid encoding the DNA polymerase mutant having a reverse transcriptase activity of the present invention. The tag may be appropriately added to a position that does not interfere with expression and tag function. It is preferable that the tag can be cleaved at a purification stage of the expressed polypeptide. Examples of such a tag capable of being cleaved include, but not limited to, tags containing nucleic acids encoding the recognition sequences of proteases for cleavage of fusion polypeptides such as Factor Xa, PreScision Protease, Thrombin, enterokinase, and TEV protease (Tobacco Etch Virus protease).

4. Method for Improving DNA Polymerase Having Reverse Transcriptase Activity of the Present Invention The method for improving a DNA polymerase having a reverse transcriptase activity of the present invention can be performed as described below. The method comprises in a DNA polymerase having a reverse transcriptase activity comprising a sequence consisting of 12 amino acids A1-A12, replacing the amino acid A3 and/or A10 by another basic amino acid residue.

In the improvement method of the present invention, first, a DNA polymerase having a reverse transcriptase activity comprising a sequence consisting of 12 amino acids A1-A12 as shown below can be selected as a candidate for a DNA polymerase before introduction of mutation.

A1 is a branched chain amino acid residue;

A2 is a hydrophilic neutral amino acid residue or a hydrophobic aliphatic amino acid residue;

A3 is a hydrophilic neutral amino acid residue;

A4 is an acidic amino acid residue or a hydrophilic neutral amino acid residue;

A5 is a branched chain amino acid residue;

A6 is a hydrophobic aliphatic amino acid residue or a hydrophilic neutral amino acid residue;

A7 is a branched chain amino acid residue;

A8 is a proline residue or a hydrophilic neutral amino acid residue;

A9 is a hydrophobic aromatic amino acid residue, a basic amino acid residue, or a hydrophilic neutral amino acid residue;

A10 is an acidic amino acid residue or a basic amino acid residue;

A11 is an acidic amino acid residue; and

A12 is a hydrophobic aliphatic amino acid residue.

An example of a method for selecting a DNA polymerase having a reverse transcriptase activity as a candidate comprises extracting a DNA polymerase comprising the amino acid sequence consisting of A1-A12 by a conventional method, for example, by computer homology search. The search can be performed using known amino acid sequence databases.

In a specific aspect of the present invention, a DNA polymerase comprising the sequence consisting of 12 amino acids in which A1 is leucine, A3 is glutamine, A5 is leucine, A7 is isoleucine, A11 is glutamic acid and A12 is alanine is preferably used as a material for introduction of mutation. In the DNA polymerase having a reverse transcriptase activity thus selected, the amino acid A3 and/or A10 is replaced by another basic amino acid residue, and thereby the improvement of the DNA polymerase is attained. Specifically, the reverse transcription activity of the DNA polymerase is enhanced, and the production amount of a reverse transcription product (cDNA) per reaction time is increased.

For the amino acid replacement as described above, it is preferable that A3 and/or A10 is replaced by an amino acid selected from the group consisting of lysine, arginine and histidine. Particularly preferred is the replacement by an arginine residue. In the improvement method of the present invention, a further mutation may be introduced into a position other than the 12 amino acid sequences of A1-A12 as long as the reverse transcriptase activity and nucleic acid amplification activity are not impaired. In the present invention, examples of the DNA polymerase having a reverse transcriptase activity to be improved include, but not limited to, DNA polymerases from *Thermus thermophilus, Thermus aquaticus, Bacillus cardotenax, Bacillus stearothermophilus,* and *Alicyclobacillus acidocaldarius,* heat-resistant polymerases from thermophilic bacteria, mesophilic DNA polymerases suitable for isothermal nucleic acid amplification methods, and altered polymerases from the above-described polymerases by amino acid replacement, insertion or deletion, and other altered polymerases derived from the above-described polymerases. In other words, the DNA polymerase having a reverse transcriptase activity to be improved may be a Pol I type or family A type DNA polymerase which originally has a low reverse transcriptase activity.

EXAMPLE

Hereinafter, the present invention will be explained in detail by means of Examples to which the scope of the present invention is not limited.

Experimental Method:

(1) Method for Preparing Tth DNA Polymerase Mutant

A nucleotide sequence of a gene encoding wild-type DNA polymerase from *Thermus thermophilus* (Tth) HB8 strain is published under NCBI Reference Sequence No. WP_011228405.1. An amino acid sequence of the DNA polymerase is shown in SEQ ID NO: 1. Artificial genes having sequences comprising mutations introduced into specific positions (a partial sequence consisting of 12 amino acids A1-A12) in the amino acid sequence were chemically synthesized. The artificial genes thus obtained were introduced into plasmid pET6xHN-N (manufactured by Takara Bio USA) using In-Fusion (registered trademark) HD Cloning Kit (manufactured by Takara Bio USA). The plasmids thus obtained had nucleotide sequences encoding Tth DNA polymerase mutants having histidine tags at the N-terminal sides.

Next, *Escherichia coli* BL21 DE3 strain (manufactured by Takara Bio Inc.) was transformed with the plasmid and cultured overnight at 37° C. on a 1.5% agarose LB plate containing 100 µg/mL ampicillin. Three single colonies were selected from the plate. The single colony was inoculated into an LB medium containing 100 µg/mL ampicillin (hereinafter referred to as an LB-AP medium), and cultured with shaking overnight at 37° C. Then, 300 µL of the culture solution was inoculated into 25 mL of an LB-AP medium and cultured with shaking overnight at 37° C. When an OD600 value of 0.6 was reached, IPTG was added at a final concentration of 1 mM to the culture solution. After culturing for induction at 37° C. for 21 hours, bacterial cells were collected.

The bacterial cells thus obtained were suspended in a solution containing 2 mL of 50 mM Tris HCl pH 8.0 (4° C.), 100 mM NaCl, 1 mM EDTA (pH 8.0) and 5% glycerol (hereinafter referred to as Buffer S). Lysozyme (manufactured by Sinopharm Chemical Reagent Co., Ltd.) was added at a final concentration of 0.1 mg/mL to the suspension. After shaking at 4° C. for 1 hour, a mixture was centrifuged at 15,000×g for 30 minutes at 4° C. A supernatant was collected. The supernatant collected was kept at 85° C. for 15 minutes and then centrifuged at 15,000×g for 30 minutes at 4° C. The supernatant after heating was concentrated about 20-fold by centrifugation using an Amicon Ultra-0.5 mL column.

The concentrate thus obtained was used as a Tth DNA polymerase mutant crude solution in experiments as described below. Regarding DNA polymerase activity, the number of units of the enzyme used was calculated on the basis of the activity of incorporating 10 nmol of all nucleotides into an acid-insoluble precipitate in a reaction solution at pH 9.3 for 30 minutes at 74° C. using an activated salmon sperm DNA as a template/primer, which is regarded as 1 U.

(2) Method for Evaluating Reverse Transcription Activity of Tth DNA Polymerase Mutants The Tth DNA polymerase mutants obtained in (1) were tested for reverse transcription reaction by the following method. For the Tth DNA polymerase mutant crude extraction solution, a reaction solution in an final volume of 50 µL was prepared, and the reaction solution contained 5×RT-PCR buffer [bicine buffer (pH 8.2) at a final concentration of 50 mM, potassium acetate at a final concentration of 115 mM, glycerol at a final concentration of 8%], manganese acetate at a final concentration of 2.5 mM, BSA at a final concentration of 0.1%, a pair of primers having nucleotide sequences shown in SEQ ID NOs: 2 and 3 at a final concentration of 0.2 µM, a probe having a nucleotide sequence shown in SEQ ID NO: 4 at a final concentration of 0.2 µM, dNTP at a final concentration of 0.3 mM, an RNA template having chain length of 4.4 kb [an RNA corresponding to a region from nucleic acid numbers 12697 to 17090 of λDNA (GenBank ACC. No. J0245.9.1), corresponding to $1 \times 10^7$ copies)], 5 U of the Tth DNA polymerase mutant prepared in Experimental method (1), and 2.5 U of Taq antibody (manufactured by Takara Bio Inc.). As a control, a reaction solution containing the wild-type Tth DNA polymerase was also prepared.

RT-PCR conditions comprised treatment at 90° C. for 30 seconds, at 60° C. for 1 minute and then at 95° C. for 1 minute, and then 45 cycles in which 1 cycle comprised 95° C. for 15 seconds and 56° C. for 45 seconds. Real-time PCR was performed using TP-990 Thermal Cycler Dice (registered trademark) Real Time System III (manufactured by Takara Bio Inc.) as a thermal cycler, and a Ct value was measured.

Example 1: Preparation of Tth DNA Polymerase Mutant

According to Experimental method (1), an artificial gene encoding a mutant protein in which glutamine at position 682 in the wild-type amino acid sequence of Tth DNA polymerase was replaced by arginine was prepared. A recombinant plasmid carrying the obtained artificial gene was prepared. According to Experimental method (1), the protein was expressed, and the expressed protein was purified. A Tth DNA polymerase mutant thus obtained had a replacement mutation from glutamine to arginine at position 682 (Q682R), which was named "b13". Similarly, a Tth DNA polymerase mutant in which glutamic acid at position 689 in the wild-type amino acid sequence of Tth DNA polymerase was replaced by arginine (E689R) (which was named "b46"), and a Tth DNA polymerase mutant in which glutamine at position 682 was replaced by arginine and glutamic acid at position 689 was replaced by arginine (Q682R+E689R) (which was named "b13b46") were prepared. The amino acid sequences and nucleic acid sequences of the mutant proteins are shown in SEQ ID NOs: 5-10.

Example 2: Reverse Transcription Activity Evaluation Test of Tth DNA Polymerase Mutant—1

The Tth DNA polymerase mutants prepared in Example 1 and the wild-type Tth DNA polymerase were evaluated for reverse transcription activity according to Experimental method (2). When the wild-type Tth DNA polymerase is commonly used, the standard reverse transcription reaction is performed at 60° C. for 30 minutes. In this example, the performance of the enzymes was compared in a short time of reverse transcription reaction at 60° C. for 1 minute. Results are shown in Table 1. Since a Ct value is inversely proportional to the starting amount of a target, the Ct value can be used to calculate the starting copy number of a DNA. For example, if the Ct value is smaller by 1 (minus 1), the amount of a DNA that can be used as a template in PCR is doubled.

TABLE 1

| | RT-PCR Ct value | |
|---|---|---|
| Mutation type | ΔCt | Conversion to starting amount of DNA template in PCR |
| No mutation, wild-type | Standard value, (0) | 1 |
| b46 | −7.2 | 146 |
| b13 | −8.5 | 360 |
| b13b46 | −10.3 | 1287 |

As shown in Table 1, the starting DNA template amounts in PCR when mutants b13, b46 and b13b46 were used were 100 to 1000 or more times the starting DNA template amount in PCR when the wild-type enzyme was used. The increase in the DNA template amount means that the amount of cDNA produced by a reverse transcription reaction before PCR increased. Thus, it was found that the mutants had a 100 to 1000 or more times higher activity in the reverse transcription reaction than the wild-type enzyme.

Example 3: Fusion Protein of PIP Box and Tth Mutant

Fusion proteins of the Tth DNA polymerase mutants described in Example 1 and a PCNA binding domain were studied. First, a fusion protein of 3 PIPs and the wild-type Tth DNA polymerase (PIP-L14-PIP-L14-PIP-L15-Tth DNA polymerase) having the amino acid sequence shown in SEQ ID NO: 11 in which the 3 PIPs comprised three PIP boxes arranged in tandem and were fused to the N-terminal side of each Tth DNA polymerase mutant was prepared according to a method as described in Example 4 of WO2017/090685. The fusion protein was named "3PIP-wild type". Similarly, fusion proteins of 3PIP with mutants b13, b46 and b13b46 described in Example 1 were prepared, and named "3PIP-b13", "3PIP-b46" and "3PIP-b13b46". In addition, a Puf PCNA D143R mutant (PCNA13), which is a polymerase-related factor that recognizes the PIP box, was prepared by a method as described in Examples of WO2007/004654.

In this Example, an RNA used as a template for the reverse transcription reaction was prepared as described below. RNAs having nucleotide sequences comprising regions that are amplified by PCR using primers for GI detection and for GII detection having the same nucleotide sequences as described in "The detection method of norovirus" (Appendix attached to Notice No. 1105001 dated on Nov. 5, 2003; final revision: 1022-No. 1 dated on Oct. 22, 2013) published by the Inspection and Safety Division, Food Safety Department, Pharmaceutical and Food Safety Bureau, Ministry of Health, Labor and Welfare (hereinafter referred to as "the official method") were prepared by a conventional method.

A reaction solution containing the RNA template prepared by the above-described method and 5×RT-PCR buffer, manganese acetate at a final concentration of 2.5 mM, BSA at a final concentration of 0.1%, the GI primer pair having nucleotide sequences shown in SEQ ID NOs: 12 and 13 as defined by the official method at a final concentration of 0.2 µM or the GII primer pair having nucleotide sequences shown in SEQ ID NOs: 14 and 15 as defined by the official method at a final concentration of 0.2 µM, a probe for GI detection having a nucleotide sequence shown in SEQ ID NO: 16 at a final concentration of 0.2 µM or a probe for GII detection having a nucleotide sequence shown in SEQ ID NO: 17 at a final concentration of 0.2 µM, dNTP at a final concentration of 0.3 mM, poly(ethylene glycol)4-nonylphenyl 3-sulfopropyl ether at a final concentration of 4%, PCNA13 at a final concentration of 850 nM, and 5 U of the above-described 3PIP-Tth DNA polymerase mutant was prepared in a final volume of 25 µL. As controls, a reaction solution containing the wild-type Tth DNA polymerase and a reaction solution containing the wild-type Tth DNA polymerase with the 3PIPs added to the N-terminal side were also prepared. RT-PCR conditions comprised treatment at 58° C. for 5 minutes and 95° C. for 30 seconds, then reaction of 5 cycles in which 1 cycle comprised 95° C. for 5 seconds and 56° C. for 1 minute, and subsequently reaction of 40 cycles in which 1 cycle comprised 90° C. for 5 seconds and 56° C. for 1 minute. The same thermal cycler as used in Example 2 was used. Results of GI detection are shown in Table 2. Similarly, results of GII detection are shown in Table 3.

TABLE 2

| Mutation type | RT-PCR Ct value ΔCt | Conversion to starting amount of DNA template in PCR |
|---|---|---|
| Wild-type (without PIP) | Standard value, (0) | 1 |
| 3PIP-wild type | −7.0 | 124 |
| 3PIP-b13 | −9.4 | 676 |
| 3PIP-b46 | −9.8 | 873 |
| 3PIP-b13b46 | −10.7 | 1698 |

TABLE 3

| Mutation type | RT-PCR Ct value ΔCt | Conversion to starting amount of DNA template in PCR |
|---|---|---|
| Wild-type | Standard value, (0) | 1 |
| 3PIP-wild type | −7.8 | 223 |
| 3PIP-b13 | −9.9 | 923 |
| 3PIP-b46 | −10.7 | 1710 |
| 3PIP-b13b46 | −12.3 | 4871 |

As shown in Tables 2 and 3, the starting DNA template amounts increased when mutants b13, b46 and b13b46 of the present invention with the PIP boxes added to the N-terminal sides were used, as compared to when the wild-type enzyme and the wild-type enzyme with the PIP boxes added to the N-terminal side were used.

Example 4: Reverse Transcription Activity Evaluation Test of Tth DNA Polymerase Mutant—2

The mutants b13 and b13b46 whose activity in the reverse transcription reaction was found to be enhanced in Example 2 were evaluated for detection of norovirus in an actual sample. A norovirus-positive stool sample was obtained from a subject who gave informed consent, suspended in PBS at about 10% (w/v), and then centrifuged at 15,000 rpm for 5 minutes. A supernatant (1 μL) thus obtained was used in a reaction as described below. A reaction solution containing 1 μL of the stool supernatant, 5×RT-PCR buffer [tricine buffer (pH 8.15) at a final concentration of 50 mM, potassium acetate at a final concentration of 50 mM, glycerol at a final concentration of 8%, DMSO at a final concentration of 1%, manganese acetate at a final concentration of 2.5 mM, BSA at a final concentration of 0.1%], the GI primer pair as defined by the official method at a final concentration of 0.2 μM, a probe for GI detection at a final concentration of 0.2 μM, dNTP at a final concentration of 0.3 mM, 5 U of the above-described 3PIP-Tth DNA polymerase mutant, poly(ethylene glycol)4-nonylphenyl 3-sulfopropyl ether at a final concentration of 4%, and 2.5 U of Taq antibody (manufactured by Takara Bio Co., Ltd.) was prepared in a final volume of 25 μL. As a control, a reaction solution containing the wild-type Tth DNA polymerase was also prepared. In the case of using Tth DNA polymerase, RT-PCR conditions comprised treatment at 90° C. for 3 minutes, 58° C. for 5 minutes or 30 minutes, and 95° C. for 30 seconds, then reaction of 5 cycles in which 1 cycle comprised 95° C. for 5 seconds and 56° C. for 30 seconds, and subsequently reaction of 40 cycles in which 1 cycle comprised 90° C. for 5 seconds and 56° C. for 30 seconds. In the case of using Tth DNA polymerase mutants, RT-PCR conditions comprised treatment at 90° C. for 3 minutes, 58° C. for 5 minutes and 95° C. for 30 seconds, then reaction of 5 cycles in which 1 cycle comprised 95° C. for 5 seconds and 56° C. for 30 seconds, and subsequently reaction of 40 cycles in which 1 cycle comprised 90° C. for 5 seconds and 56° C. for 30 seconds. The same thermal cycler as used in Example 2 was used.

As a result of the above experiments, norovirus GI in stools was detected using the Tth DNA polymerase only when the reverse transcription reaction was performed 58° C. for 30 minutes. On the other hand, norovirus GI in stools was detected using the mutants b13 and b13b46 of the present invention even when the reverse transcription reaction was performed at 58° C. for a short period of 5 minutes. These results show that the mutants of the present invention retain the enhanced activity in the reverse transcriptase reaction even when they are used for detection in actual samples.

Example 5: Reverse Transcription Activity Evaluation Test of Tth DNA Polymerase Mutant—3

The Tth DNA polymerase mutants of the present invention were compared to Tth DNA polymerase mutants that were previously reported to enable a high-temperature and efficient reverse transcription reaction. Crude enzyme solutions of the Tth DNA polymerase mutants were prepared by Experimental method (1), according to Japanese Patent No. 3844975. Specifically, since position 681 in the amino acid sequence of Taq DNA polymerase (Genbank Acc. No. BAA06775.1) corresponds to position 683 in the amino acid sequence of Tth DNA polymerase based on the amino acid sequence described in NCBI Reference Sequence No. WP 0112288405, glutamic acid at position 683 in the amino acid sequence was replaced by phenylalanine, lysine, leucine, arginine or tyrosine to prepare Tth DNA polymerase mutants. These amino acid mutants were named mutants E683F, E683K, E683L, E683R, and E683Y.

The evaluation was performed by Experimental method (2) as described above, except that the reverse transcription reaction time was changed from 1 minute to 2 minutes at 60° C. Results are shown in Table 4.

TABLE 4

| Mutation type | RT-PCR Ct value ΔCt | Conversion to starting amount of DNA template in PCR |
|---|---|---|
| b13b46 | Standard value, (0) | 1 |
| E683F | No amplification | |
| E683K | +1.22 | 0.43 |
| E683L | No amplification | |
| E683R | +3.81 | 0.07 |
| E683Y | No amplification | |

As shown in Table 4, the Tth DNA polymerase mutants comprising replacement of glutamic acid at position 683 could not produce an amplified product from the template, or produced higher Ct values than the Tth DNA polymerase mutant of the present invention. The results mean that the starting DNA template amount at the start of PCR decreased, in other words, the amount of cDNA produced by the reverse transcription reaction before PCR was about ½ or less, as compared to the mutant of the present invention. Thus it was found that the mutant of the present invention is superior in the reverse transcription reaction activity to the mutants prepared by the prior art technique.

Experimental Method
(3) Method for Preparing Bca DNA Polymerase Mutant

A nucleotide sequence of a gene encoding wild-type DNA polymerase from *Bacillus caldoteneax* (Bca) is published under NCBI Reference Sequence No. NZ_CP02574.1. An amino acid sequence of the DNA polymerase is shown in SEQ ID NO: 23. Artificial genes having sequences comprising mutations introduced into specific positions (a partial sequence consisting of 12 amino acids A1-A12) in the amino acid sequence were chemically synthesized. According to Experimental method (1), plasmids containing the genes encoding Bac DNA polymerase mutants with histidine tags at the N-terminal sides were prepared.

Next, *Escherichia coli* BL21 DE3 strain (manufactured by Takara Bio Inc.) was transformed with the plasmid and cultured overnight at 37° C. on a 1.5% agarose LB plate containing 100 µg/mL ampicillin. Three single colonies were selected from the plate. the single colony was inoculated into an LB medium containing 100 µg/mL ampicillin (hereinafter referred to as an LB-AP medium), and cultured with shaking overnight at 37° C. Then, 30 mL of the culture solution was inoculated into 3 L of an LB-AP medium and cultured with shaking overnight at 37° C. When an OD600 value of 0.6 was reached, IPTG was added at a final concentration of 1 mM to the culture solution. After culturing for induction at 37° C. for 4 hours, bacterial cells were collected.

The bacterial cells (3 g) thus obtained were suspended in 12 mL of a buffer (50 mM Tris HCl pH 7.0 (4° C.), 4 µM PMSF, 1 mM DTT, 10% glycerol), stirred with Sonic 180 W for 10 minutes, and then centrifuged at 10,000 rpm for 30 minutes at 4° C. A supernatant was collected and heated at 60° C. for 30 minutes. The supernatant after the heat treatment was cooled on ice for 30 minutes and then centrifuged at 11,000 rpm for 30 minutes (4° C.) to recover a supernatant. The supernatant thus obtained was subjected to DEAE Sepharose Fast Flow (manufactured by GE Healthcare), CM Sephadex Fast Flow (manufactured by GE Healthcare), Sephadex-G100, Heparin Sepharose (manufactured by GE Healthcare), and then Q Sepharose (manufactured by GE Healthcare) to prepare a purified solution of Bca DNA polymerase mutant protein. The purified solution was used in tests as described below. Regarding DNA polymerase activity, the number of units of the enzyme used was calculated on the basis of the activity of incorporating 10 nmol of all nucleotides into an acid-insoluble precipitate in a reaction solution at pH 9.3 for 30 minutes at 74° C. using an activated salmon sperm DNA as a template/primer, which is regarded as 1 U.

Experimental Method
(4) Method for Preparing Aac DNA Polymerase Mutant

A nucleotide sequence of a gene encoding wild-type DNA polymerase from *Alicyclobacillus acidocaldarius* (Aac) is published under NCBI Reference Sequence No. AB275481.1. An amino acid sequence of the DNA polymerase is shown in SEQ ID NO: 24. Artificial genes having sequences comprising mutations introduced into specific positions (a partial sequence consisting of 12 amino acids A1-A12) in the amino acid sequence were chemically synthesized. According to Experimental method (1), plasmids containing the genes encoding Aac DNA polymerase mutants with histidine tags at the N-terminal sides were prepared.

Next, *Escherichia coli* BL21 DE3 strain was transformed with the plasmid and cultured in the same manner as described in Experimental method (3). Thus the bacterial cells were collected.

The bacterial cells (3 g) thus obtained were purified in the same manner as described in Experimental method (3) to prepare a purified solution of the Aac DNA polymerase mutant. The purified solution was used in tests as described below. The number of units of the enzyme used was calculated in the same manner as in the case of Bca DNA polymerase.

Experimental Method
(5) Method for Preparing Taq DNA Polymerase Mutant

A nucleotide sequence of a gene encoding wild-type DNA polymerase from *Thermus aquaticus* (Taq) is published under NCBI Reference Sequence No. D32013.1. An amino acid sequence of the DNA polymerase is shown in SEQ ID NO: 25. Artificial genes having sequences comprising mutations introduced into specific positions (a partial sequence consisting of 12 amino acids A1-A12) in the amino acid sequence were chemically synthesized. According to Experimental method (1), plasmids containing the genes encoding Taq DNA polymerase mutants with histidine tags at the N-terminal sides were prepared.

Next, *Escherichia coli* BL21 DE3 strain was transformed with the plasmid and cultured in the same manner as described in Experimental method (3). Thus the bacterial cells were collected.

The bacterial cells (13 g) thus obtained were suspended in 39 mL of a buffer [100 mM Tris HCl pH 7.5 (4° C.), 200 mM EDTA pH 7.5, 2.4 µM PMSF], stirred with Sonic 180 W for 10 minutes, and then centrifuged at 12,000 rpm for 30 minutes at 4° C. A supernatant was collected, and 1.34 g of ammonium sulfate and 0.64 mL of 10% PEI were added to the supernatant. After stirring for 30 minutes (4° C.), a mixture was centrifuged for 30 minutes (4° C.). Then, a supernatant was collected. The supernatant was heated at 75° C. for 15 minutes, cooled on ice for 30 minutes, and then centrifuged at 35,000 rpm for 60 minutes (4° C.) to recover a supernatant. The supernatant thus obtained was purified by using Phenyl Sepharose Cl-4B (GE Healthcare). The number of units of the enzyme used was calculated in the same manner as in the case of Bca DNA polymerase.

Experimental Method
(6) Method for Evaluating Reverse Transcription Activity of Bca, Aac and Taq DNA Polymerase Mutants The polymerases (Pol) activity of the Bca, Aac and Taq DNA polymerase mutants obtained in (3), (4) and (5) was measured. For the measurement of Pol activity, a reaction solution containing TAPS buffer (pH 9.3, 25° C.) at a final concentration of 25 mM, KCl at a final concentration of 50 mM, $MgCl_2$ at a final concentration of 2 mM, DTT at a final concentration of 0.1 mM, dATP, dGTP and dCTP at each final concentration of 200 µM, [3H]-dTTP at a final concentration of 100 µM, and activated salmon sperm DNA at a final concentration of 0.25 mg/ml was prepared. Specifically, activity of incorporating 10 nmol of all nucleotides into an acid-insoluble precipitate at 74° C. for 30 minutes in the reaction solution for measurement was measured using the activated salmon sperm DNA as a template/primer, and the activity measured was regarded as 1 U.

Next, the reverse transcription activity of the Bca, Aac and Taq DNA polymerase mutants obtained in (3), (4) and (5) was measured. For the measurement of reverse transcription activity, a reaction solution containing 50 mM Tris-HCl pH 8.3 (37° C.), 5 mM Tris-HCl pH 7.5 (37° C.), 85 mM KCl, 8 mM MgCl$_2$, 10 mM DTT, 0.1% NP-40, 0.02 mg/ml Poly(A), 2.5 mM dTTP, and 100 µCi/ml [3H]-dTTP was prepared. Specifically, enzymatic activity of incorporating 1 nmol of [3H]-dTTP at 37° C. for 10 minutes in the reaction solution for measurement was measured using Poly(rA) •oligo(dT)12-18 as a template/primer, and the activity measured was regarded as 1 U.

Experimental Method
(7) Method for Evaluating Reverse Transcription Activity of Bca, Aac and Taq DNA Polymerase Mutants The Bca, Aac and Taq DNA polymerase mutants obtained in (3), (4) and (5) were tested for reverse transcription reaction by the following method. In this test, a part of the components of BcaBEST (trademark) RNA PCR Kit (manufactured by Takara Bio Inc.) was used. Specifically, for each DNA polymerase mutant purification solution, 2×Bca 1st Buffer attached to the kit, 25 mM MgSO$_4$, RNase inhibitor (40 U/µl), 10 mM dNTP, a reverse transcription primer having a nucleotide sequence shown in SEQ ID NO: 26 at a final concentration of 0.5 µM, dNTP at a final concentration of 500 µM, HL60 total RNA (manufactured by Takara Bio Inc.) as a template at a final concentration of 10 ng/µL, and 0.5 µL of the purified solution of Bca, Aac or Taq DNA polymerase mutant prepared by Experimental method (3), (4) or (5) were mixed to prepare 10 µL of a reverse transcription reaction solution. As a control, a reaction solution containing wild-type Bca, Aac or Taq DNA polymerase was also prepared.

Reverse transcription conditions comprised treatment at 65° C. for 60 seconds, at 55° C. for 5 minutes, and at 95° C. for 2 minutes. As a thermal cycler, TP-990 Thermal Cycler Dice (registered trademark) Real Time System III (manufactured by Takara Bio Inc.) was used.

A cDNA solution thus obtained was subjected to real-time PCR. Real-time PCR was performed using RR420A TB Green (registered trademark) Premix Ex Taq (trademark) (Tli RNase H Plus) (manufactured by Takara Bio Inc.). A PCR reaction solution containing a forward primer having a nucleotide sequence shown in SEQ ID NO: 26 at a final concentration of 0.2 µM, a reverse primer having a nucleotide sequence shown in SEQ ID NO: 27 at a final concentration of 0.2 µM, and 1 µL of cDNA obtained by the above-described reverse transcription reaction was prepared. The PCR reaction solution (25 µL per one reaction) was subjected to real-time PCR reaction.

PCR conditions comprised initial denaturation at 90° C. for 30 seconds and then reaction of 40 cycles in which 1 cycle comprised 95° C. for 5 seconds and 60° C. for 30 seconds. Real-time PCR was performed using TP-990 Thermal Cycler Dice (registered trademark) Real Time System III (manufactured by Takara Bio Inc.) as a thermal cycler, and a Ct value was measured.

Example 6: Reverse Transcription Activity Evaluation Test of Bca, Aac and Taq Mutants—1

Evaluation test 1 was performed using the Bca, Aac and Taq DNA polymerase mutants obtained in (3), (4) and (5) by the method described in Experimental method (6). Results are shown in Table 5. Each DNA polymerase mutant b13b46 comprised mutations corresponding to the mutations "Q682R+E689R" of Tth DNA polymerase mutant b13b46 (in other words, amino acids at positions corresponding to positions 682 and 689 in the amino acid sequence of Tth DNA polymerase were replaced by arginine).

TABLE 5

| Mutation type | Pol activity (U/µg) | Reverse transcription activity (U/µg) | RT\Pol activity ratio |
| --- | --- | --- | --- |
| Bca native-type | 127.9 | 25.5 | 1 |
| Bca mutant (b13b46) | 194.6 | 79.4 | 2 |
| Aac native-type | 73.9 | 8.5 | 1 |
| Aac mutant (b13b46) | 88.8 | 38.8 | 4 |
| Taq native-type | 82.26 | 1.1 | 1 |
| Taq mutant (b13b46) | 82.01 | 9.5 | 9 |

As shown in Table 5, the Bca (b13b46) mutant prepared in contrast to the Bca native-type had an enhanced reverse transcription activity while maintaining the polymerase activity. The reverse transcription activity of the Bca (b13b46) mutant was enhanced by about 2 times as compared to the native-type. In the case of Aac, the reverse transcription activity of the Aac (b13b46) mutant was enhanced by about 4 times as compared to the native-type while the polymerase activity was maintained. In the case of Taq, the reverse transcription activity of the Taq (b13b46) mutant was enhanced by about 9 times as compared to the native-type while the polymerase activity was maintained.

Example 7: Reverse Transcription Activity Evaluation Test of Bca, Aac and Taq Mutants—2

The amounts of cDNAs synthesized using the Bca, Aac and Taq DNA polymerase mutants obtained in (3), (4) and (5) were confirmed to evaluate the reverse transcription activity.

Evaluation test 2 was performed by the method described in Experimental method (7). Results are shown in Table 6.

TABLE 6

| | RT-PCR Ct value | |
| --- | --- | --- |
| Mutation type | ΔCt | Conversion to starting amount of DNA template in PCR |
| Bca native-type | Standard value, (0) | 1 |
| Bca mutant (b13b46) | −10.18 | 1160 |
| Aac native-type | Standard value, (0) | 1 |
| Aac mutant (b13b46) | −9.35 | 653 |
| Taq native-type | Standard value, (0) | 1 |
| Taq mutant (b13b46) | −9.02 | 519 |

As shown in Table 6, the starting DNA template amount in PCR when each mutant was used was 510 to 1000 or more times that when the wild-type enzyme was used. The increase in the DNA template amount means that the amount of cDNA produced by reverse transcription reaction before PCR increased. Thus, it was found that the mutants had a 510 to 1000 or more times higher activity in the reverse transcription reaction than the wild-type enzymes. It was also found that the reverse transcriptase activity of DNA polymerases classified into Pol I type or Family A type can be improved according to the present invention.

INDUSTRIAL APPLICABILITY

According to the present invention, a DNA polymerase having a reverse transcriptase activity which is suitable for performing a reverse transcription reaction and a nucleic acid amplification reaction in the same container is provided. Use of the DNA polymerase enables an efficient reverse transcription reaction even when an RNA having rigid secondary structure, which has been difficult to be reverse transcribed, is used as a template. Further, the increased efficiency of reverse transcription reaction enables detection in a shorter time and with similar or higher sensitivity than conventional enzymes when a reverse transcription reaction and a nucleic acid amplification reaction are continuously performed in the same container. Thus, the DNA polymerase having a reverse transcriptase activity of the present invention is useful in a wide range of fields including genetic engineering, biology, medical science, and agriculture.

The invention claimed is:

1. A mutant of a wildtype DNA polymerase derived from *Thermus thermophilus*, the wildtype DNA polymerase having reverse transcriptase activity
    wherein the wildtype DNA polymerase is the amino acid sequence set forth in SEQ ID NO:1, and comprises a sequence consisting of 12 amino acids A1-A12 set forth in SEQ ID NO: 18;
    wherein the mutant comprises a sequence consisting of the 12 amino acids A1-A12, except that either (i) A3 is replaced by a basic amino acid residue, or (ii) A3 and A10 are each replaced by a basic amino acid residue,
    wherein, in the portion outside the 12 amino acid sequence of A1-A12, the mutant has at least 90% amino acid sequence identity to the amino acid sequence set forth in SEQ ID NO: 1, and wherein the reverse transcriptase activity in the mutant is improved relative to the wildtype DNA polymerase.

2. A kit containing the mutant according to claim 1.

3. A composition comprising the mutant according to claim 1.

4. The mutant according to claim 1, wherein, in the portion outside the 12 amino acid sequence of A1-A12, the mutant has at least 95% amino acid sequence identity to the amino acid sequence set forth in SEQ ID NO: 1.

5. The mutant according to claim 1, wherein the mutant comprises either (i) A3 in the wildtype DNA polymerase is replaced with arginine, or (ii) A3 and A10 in the wildtype DNA polymerase are each replaced with arginine.

* * * * *